(12) United States Patent
Hopkins et al.

(10) Patent No.: US 11,370,769 B2
(45) Date of Patent: Jun. 28, 2022

(54) TRPC5 INHIBITORS AND METHODS OF USING SAME

(71) Applicants: BOARD OF REGENTS OF THE UNIVERSITY OF NEBRASKA, Lincoln, NE (US); The Brigham and Women's Hospital, Inc., Boston, MA (US)

(72) Inventors: Corey Hopkins, Omaha, NE (US); Anna Greka, Boston, MA (US)

(73) Assignees: Board of Regents of the University of Nebraska, Lincoln, NE (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/644,188

(22) PCT Filed: Sep. 7, 2018

(86) PCT No.: PCT/US2018/049905
§ 371 (c)(1),
(2) Date: Mar. 4, 2020

(87) PCT Pub. No.: WO2019/051197
PCT Pub. Date: Mar. 14, 2019

(65) Prior Publication Data
US 2020/0216411 A1    Jul. 9, 2020

Related U.S. Application Data

(60) Provisional application No. 62/555,219, filed on Sep. 7, 2017.

(51) Int. Cl.
*C07D 401/04* (2006.01)
*A61P 13/12* (2006.01)
*C07D 401/12* (2006.01)

(52) U.S. Cl.
CPC ............ *C07D 401/04* (2013.01); *A61P 13/12* (2018.01); *C07D 401/12* (2013.01)

(58) Field of Classification Search
CPC combination set(s) only.
See application file for complete search history.

(56) References Cited

U.S. PATENT DOCUMENTS

| 9,018,208 | B2 * | 4/2015 | Christos | A61P 29/00 514/248 |
|---|---|---|---|---|
| 2010/0240663 | A1 | 9/2010 | Christos et al. | |
| 2016/0039828 | A1 | 2/2016 | Chappie et al. | |

OTHER PUBLICATIONS

Akilesh et al., Arhgap24 inactivates Rac1 in mouse podocytes, and a mutant form is associated with familial focal segmental glomerulosclerosis. J Clin Invest 121, 4127-4137 (2011).
Berge et al., Pharmaceutical Salts, J. Pharm. Sci., 66:1-19 (1977).
Bezzerides, et al., Rapid vesicular translocation and insertion of TRP channels. Nature Cell Biol 6, 709-720 (2004).
Brown et al., Genetic testing for nephrotic syndrome and FSGS in the era of next-generation sequencing. Kidney Int 85, 1030-1038 (2014).
Buvall et al., Synaptopodin Is a Coincidence Detector of Tyrosine versus Serine/Threonine Phosphorylation for the Modulation of Rho Protein Crosstalk in Podocytes. J Am Soc Nephrol (2016).
Cheney et al., The novel compound LOE 908 attenuates acute neuromotor dysfunction but not cognitive impairment or cortical tissue loss following traumatic brain injury in rats, J. Neurotrauma, 17(1):83-91 (2000).
D'Agati et al., Focal segmental glomerulosclerosis. New Engl J Med 365, 2398-2411 (2011).
Eckel et al. "TRPC6 Enhances Angiotensin II-induced Albuminuria." J Am Soc Nephrol 22(3): 526-535 (2011).
Etcheberrigaray et al., Calcium responses in fibroblasts from asymptomatic members of Alzheimer's disease families, Neurobiol. Dis., 5(1):37-45 (1998).
Freichel et al., Lack of an endothelial store-operated Ca2+ current impairs agonist-dependent vasorelaxation in TRP4-/-mice. Nature Cell Biol 3, 121-127 (2001).
Garrett et al., Time-course genetic analysis of albuminuria in Dahl salt-sensitive rats on low-salt diet. J Am Soc Nephrol 14, 1175-1187 (2003).
Gee et al., ARHGDIA mutations cause nephrotic syndrome via defective RHO GTPase signaling. J Clin Invest 123, 3243-3253 (2013).
Gee et al., KANK deficiency leads to podocyte dysfunction and nephrotic syndrome. J Clin Invest 125, 2375-2384 (2015).
Gee et al., Mutations in EMP2 cause childhood-onset nephrotic syndrome. Am J Hum Genet 94, 884-890 (2014).
Gibson et al., Calcium stores in cultured fibroblasts and their changes with Alzheimer's disease, Biochim. Biophys. Acta, 1316(2):71-7 (1996).
Greka et al., Cell biology and pathology of podocytes. Annual Rev Physiol 74, 299-323 (2012).
Guo et al., Alzheimer's PS-1 mutation perturbs calcium homeostasis and sensitizes PC12 cells to death induced by amyloid β-peptide, NeuroReport, 8(1):379-383 (1996).
Hoffmann et al., Angiotensin II Type 1 Receptor Overexpression in Podocytes Induces Glomerulosclerosis in Transgenic Rats. J Am Soc Nephrol 15, 1475-1487 (2004).
Hofmann et al., Direct activation of human TRPC6 and TRPC3 channels by diacylglycerol. Nature 397, 259-263 (1999).
Hsu et al., Mechanisms of angiotensin II signaling on cytoskeleton of podocytes. J Mol Med 86, 1379-1394 (2008).
Inrig et al., The landscape of clinical trials in nephrology: a systematic review of Clinicaltrials.gov. Am J Kidney Diseases 63, 771-780 (2014).
International Application No. PCT/US18/49905, International Search Report and Written Opinion, dated Jan. 18, 2019.
Ito et al., Internal Ca2+ mobilization is altered in fibroblasts from patients with Alzheimer disease, Proc. Natl. Acad. Sci. USA, 91(2):534-8 (1994).

(Continued)

*Primary Examiner* — Heidi Reese
(74) *Attorney, Agent, or Firm* — Marshall, Gerstein & Borun LLP

(57) ABSTRACT

Provided herein are TRPC5 inhibitors and methods of using the same, e.g., to protect podocytes and/or treat kidney disease.

14 Claims, 6 Drawing Sheets

(56) References Cited

OTHER PUBLICATIONS

Jha et al., Chronic kidney disease: global dimension and perspectives. Lancet 382, 260-272 (2013).
Kriz et al., A potential role for mechanical forces in the detachment of podocytes and the progression of CKD. J Am Soc Nephrol 26, 258-269 (2015).
Leissring et al., Alzheimer's presenilin-1 mutation potentiates inositol 1,4,5-trisphosphate-mediated calcium signaling in Xenopus oocytes, J. Neurochem., 72(3):1061-8 (1999).
Leissring et al., Calsenilin reverses presenilin-mediated enhancement of calcium signaling, Proc. Natl. Acad. Sci. USA, 97(15):8590-3 (2000).
Leissring et al., Capacitative calcium entry deficits and elevated luminal calcium content in mutant presenilin-1 knockin mice, J. Cell Biol., 149(4):793-8 (2000).
Leissring et al., Presenilin-2 mutations modulate amplitude and kinetics of inositol 1, 4,5-trisphosphate-mediated calcium signals, J. Biol. Chem., 274(46):32535-8 (1999).
Lek et al., Analysis of protein-coding genetic variation in 60,706 humans. Nature 536, 285-291 (2016).
Love et al., Moderated estimation of fold change and dispersion for RNA-seq data with DESeq2. Genome Biol 15, 550 (2014).
Miller et al., Identification of ML204, a novel potent antagonist that selectively modulates native TRPC4/C5 ion channels. J Biol Chem 286, 33436-33446 (2011).
Pierce et al., Seven-transmembrane receptors. Nat Rev Mol Cell Biol 3, 639-650 (2002).
PubChem-CID-118875414, Create Date: Apr. 9, 2016, p. 4, Fig.
PubChem-CID-561409, create date: Mar. 27, 2005, p. 4, Fig.
Rapp, Dahl salt-susceptible and salt-resistant rats. A review. Hypertens 4, 753-763 (1982).
Riccio et al., Essential role for TRPC5 in amygdala function and fear-related behavior. Cell 137, 761-772 (2009).
Richter et al., Clemizole hydrochloride is a novel and potent inhibitor of transient receptor potential channel TRPC5. Mol Pharmacol 86, 514-521 (2014).
Richter et al., Riluzole activates TRPC5 channels independently of PLC activity. Br J Pharmacol 171, 158-170 (2014).
Riehle et al., TRPC6 G757D Loss-of-Function Mutation Associates with FSGS. J Am Soc Nephrol 27, 2771-2783 (2016).
Schaldecker et al., Inhibition of the TRPC5 ion channel protects the kidney filter. J Clin Invest 123, 5298-5309 (2013).
Sharma et al. "Adiponectin regulates albuminuria and podocyte function in mice." J Clin Invest 118(5): 1645-1656 (2008).
Steffes et al., Glomerular cell number in normal subjects and in type 1 diabetic patients. Kidney Int 59, 2104-2113. (2001).
Tarazona et al., Data quality aware analysis of differential expression in RNA-seq with NOISeq R/Bioc package. Nucleic Acids Res 43, e140 (2015).
Tian et al., Antagonistic regulation of actin dynamics and cell motility by TRPC5 and TRPC6 channels, Science Signaling, 3(145):ra77 (2010).
Weins et al., Dendrin ablation prolongs life span by delaying kidney failure. Am J Pathol 185, 2143-2157 (2015).
Wieder et al., Calcium, TRPC channels, and regulation of the actin cytoskeleton in podocytes: towards a future of targeted therapies. Pediatr Nephrol, (2015).
Wu et al., Subcellular targeting of oxidants during endothelial cell migration. J Cell Biol 171, 893-904 (2005).
Yamada et al., Mechanism underlying the efficacy of combination therapy with losartan and hydrochlorothiazide in rats with salt-sensitive hypertension. Hypertens Res 34, 809-816 (2011).
Yoo et al., Presenilin-mediated modulation of capacitative calcium entry, Neuron., 27(3):561-72 (2000).
You et al. "Metabolomics Reveals a Key Role for Fumarate in Mediating the Effects of NADPH Oxidase 4 in Diabetic Kidney Disease." J Am Soc Nephrol 27(2): 466-481 (2016).
Yu et al., A role for genetic susceptibility in sporadic focal segmental glomerulosclerosis. J Clin Invest 126, 1603 (2016).
Zicha et al., Age-dependent salt hypertension in Dahl rats: fifty years of research. Physiol Res 61 Suppl 1, S35-87 (2012).
Butler et al., Regioselective synthesis of 3-aminoimidazo[1,2-a]-pyrimidines under continuous flow conditions, J. Org. Chem., 79(21):10196-202 (2014).
Carballares et al., Regioselective two step synthesis of 3-substituted 2-aminoimidazo[1,2-alpha]pyrimidines, Tetrahedron Lett., 48(11):2041-5 (2007).
European Patent Application No. 18853163.6, Extended European Search Report, dated Jun. 16, 2021.
Richter et al., Clemizole hydrochloride is a novel and potent inhibitor of transient receptor potential channel TRPC5, Mol. Pharmacol., 86(5):514-21 (2014).
Thompson et al., Regioselective, solvent-free synthesis of 3-aminoimidazo[1,2-alpha]pyrimidines under microwave irradiation promoted by zeolite HY, Synlett, 2008(20):3183-7 (2008).
Zhou et al., A small-molecule inhibitor of TRPC5 ion channels suppresses progressive kidney disease in animal models, Science, 358(6368):1332-6 (2017).
Prakriya et al., Store-Operated Calcium Channels, Physiol. Rev., 95(4):1383-436 (2015).
Takano et al., An X-linked channelopathy with cardiomegaly due to a CLIC2 mutation enhancing ryanodine receptor channel activity, Hum. Mol. Genet., 21(20):4497-507 (2012).
Garcia-Elias et al., Phosphatidylinositol-4,5-biphosphate-dependent rearrangement of TRPV4 cytosolic tails enables channel activation by physiological stimuli, Proc. Natl. Acad. Sci. USA, 110(23):9553-8 (2013).
Kung et al., A novel role for the apoptosis inhibitor ARC in suppressing TNFa-induced regulated necrosis, Cell Death Differ., 21(4):634-44 (2014).
Jaffrey et al., CAPON: a protein associated with neuronal nitric oxide synthase that regulates its interactions with PSD95, Neuron., 20(1):115-24 (1998).
Rhee et al., Cell signaling. H2O2, a necessary evil for cell signaling, Science, 312(5782):1882-3 (2006).

\* cited by examiner (to be continued)

G (continuation)

TRPC5 INHIBITORS AND METHODS OF USING SAME

STATEMENT OF GOVERNMENT SUPPORT

This invention was made with government support under R01 DK095045, R01 DK099465, and R01 DK 103658, each awarded by the National Institutes of Health. The government has certain rights in the invention.

BACKGROUND

Progressive chronic kidney diseases affect an estimated 26 million people in the United States and more than 200 million worldwide, yet drug development has been stagnant for more than 40 years (1, 2). The leading histopathologic diagnosis associated with progressive chronic kidney disease is FSGS (3). The most severe form of FSGS, affecting 50,000 patients in the U.S. alone, is associated with the nephrotic syndrome, which is diagnosed based on proteinuria, the spilling of essential proteins into the urine, and histopathologic findings including scarring in large segments of the glomerulus, the filtering unit of the kidney (3). This glomerular scarring is due to injury and loss of terminally differentiated cells of the kidney filter, the podocytes (3, 4). Both the proteinuria and the histopathologic abnormalities contribute to patient symptoms (such as severe edema and shortness of breath) and increase the risk of kidney failure, heart failure and premature death (3). Current therapy for FSGS consists of off-label use of non-specific medications, which do not alter the progression of disease and carry significant toxicities (3).

Inherited, familial forms of the disease currently account for approximately 5-10% of FSGS patients worldwide (5). The majority of known mutations occur in genes that encode regulators of the actin cytoskeleton (5). Two recently identified genes for inherited FSGS encode regulators of the actin modulator Rac1, ARHGAP24 (6) and ARHGDIA (7). De novo sporadic mutations conferring susceptibility to FSGS also cluster in genes that encode regulators of Rac1, such as ARHGEF17 (8). In all cases, the functional consequence of these mutations is excess Rac1 signaling in podocytes (6-8).

At the cellular level, an important consequence of excess Rac1 signaling in podocytes is the vesicular insertion of TRPC5 ion channels into the plasma membrane (9, 10). Once inserted, TRPC5 channels can be activated by receptors such as the Angiotensin Type 1 Receptor (AT1R) and, once active, TRPC5 channels mediate $Ca^{2+}$ influx into the podocyte (10). This in turn triggers further Rac1 activation, resulting in a positive feedback loop that promotes podocyte cytoskeletal remodeling (10, 11). While these studies show that podocytes with an aberrant cytoskeleton are associated with acute (and reversible) changes to the kidney filter barrier (11), nothing is known about the pathophysiologic role of the Rac1-TRPC5 pathway in the onset and progression of FSGS, which is characterized by podocyte loss. Given that many lines of evidence from human genetics (6-8) and cell biology (10, 11) converge on Rac1-TRPC5 as an injury pathway of interest (9-12), it is important to know whether this pathway responsible for disease progression in FSGS, and if so, if it can be blocked for therapeutic benefit.

SUMMARY

Provided herein are compounds that inhibit TRPC5. In various cases, the compound, or pharmaceutically acceptable salt thereof, has a structure of formula (I) or (II):

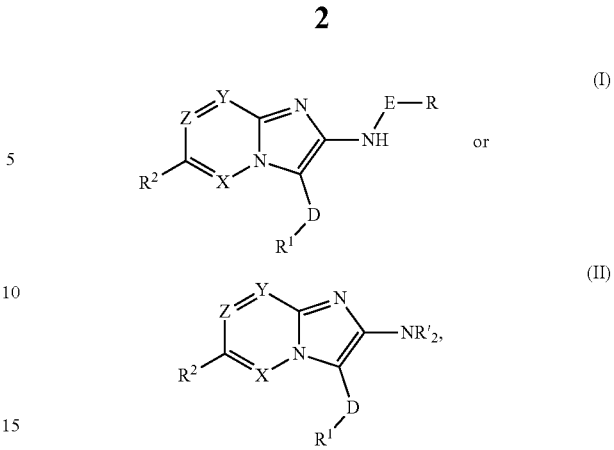

wherein X, Y, and Z are each independently N or $CR^2$; D is a bond, $C_1$-$C_4$alkylene, $C_0$-$C_4$alkylene-O—, or $C_0$-$C_4$alkylene-$NR^3$—; E is a bond, $C_1$-$C_4$alkylene, $C_1$-$C_4$alkylene-O—, $SO_2$, or C(O); R comprises $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O, and R is optionally substituted with one, two or three substituents selected from halo, CN, $C_1$-$C_6$alkyl, $C_1$-$C_6$haloalkyl, and $C_3$-$C_6$cycloalkyl; $R^1$ comprises $C_1$-$C_4$ alkyl, $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O, and $R^1$ is optionally substituted with one, two, or three substituents selected from halo, CN, $C_1$-$C_6$alkyl, $C_1$-$C_6$haloalkyl, and $C_3$-$C_6$cycloalkyl; each $R^2$ is independently H, halo, $C_1$-$C_5$alkyl, $C_1$-$C_5$haloalkyl, or $C_3$-$C_{12}$cycloalkyl; $R^3$ is H, $C_1$-$C_6$ alkyl, $C_6$-$C_{12}$ aryl, or $C_3$-$C_{10}$ heteroaryl containing 1 to 3 ring heteroatoms selected from N, S, and O; and each R' together with the nitrogen atom to which they are attached form a 3-10 membered heterocycloalkyl containing 0 to 3 additional ring heteroatoms selected from N, S, and O, and the heterocycloalkyl is optionally substituted with one, two or three substituents selected from halo, CN, $C_1$-$C_6$alkyl, $C_1$-$C_6$haloalkyl, and $C_3$-$C_6$cycloalkyl. In some cases, X is N, and Y and Z are each $CR^2$. In various cases, Z is N, and X and Y are each $CR^2$. In some cases, Y is N, and X and Z are each $CR^2$. In some cases, X, Y, and Z are each $CR^2$. In various cases, $R^1$ is $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O. In various cases, each $R^2$ is H. In various cases, at least one $R^2$ is halo. In various cases, D is a bond. In various cases, D is $C_1$-$C_4$alkylene, $C_0$-$C_4$alkylene-O—, or $C_0$-$C_4$alkylene-$NR^3$. In various cases, D is $CH_2$ or $CH_2CH_2$. In various cases, D is $CH_2CH_2O$. In various cases, E is $C_1$-$C_4$alkylene or $C_1$-$C_4$alkylene-O. In various cases, E is $CH_2$. In various cases, E is a bond. In various cases, E is C(O) or $SO_2$. In various cases, R comprises $C_3$-$C_{10}$ heteroaryl containing 1 to 3 ring heteroatoms selected from N, S, and O or $C_3$-$C_{10}$ heterocycloalkyl containing 1 to 3 ring heteroatoms selected from N, S, and O. In various cases, R comprises $C_3$-$C_{10}$ heteroaryl containing 1 to 3 ring heteroatoms selected from N, S, and O. In various cases, R comprises furyl, thienyl, thiazolyl, oxazolyl, oxadiazolyl, thiadiazolyl, pyridyl, pyridazinyl, pyrimidinyl, pyrazinyl, pyranyl, tetrahydrofuryl, or tetrahydropyranyl. In various cases, R comprises phenyl. In some cases, the compound is a compound of Formula (II). In some cases, —NR'$_2$ forms a 5-6 membered heterocycloalkyl ring. In some cases, the —NR'$_2$ heterocycloalkyl ring is substituted with one, two or three substituents selected from halo, CN, $C_1$-$C_6$alkyl, $C_1$-$C_6$haloalkyl, and $C_3$-$C_6$cycloalkyl. In some cases, the —NR'$_2$ heterocycloalkyl ring is unsubstituted. In various cases, R$^1$ comprises phenyl. In various cases, R$^1$ comprises $C_3$-$C_{10}$ heteroaryl containing 1 to 3 ring heteroatoms selected from N, S, and O or $C_3$-$C_{10}$ heterocycloalkyl containing 1 to 3 ring heteroatoms selected from N, S, and O. In various cases, R$^1$ comprises furyl, thienyl, thiazolyl, oxazolyl, oxadiazolyl, thiadiazolyl, pyridyl, pyridazinyl, pyrimidinyl, pyrazinyl, pyranyl, tetrahydrofuryl, tetrahydropyranyl, morpholinyl, piperadinyl, thiomorpholinyl, or piperazinyl. In various cases, R$^1$ is $C_1$-$C_4$ alkyl. In various cases, the compound is a compound as recited in Table 1. In various cases, the compound is in the form of a pharmaceutically acceptable salt. Further provided are pharmaceutical compositions comprising a compound as disclosed herein and a pharmaceutically acceptable carrier.

Further provided is a method of inhibiting TRPC5 comprising contacting TRPC5 with a compound as disclosed herein in an amount sufficient to inhibit TRPC5. In some cases, the compound selectively inhibits TRPC5 compared to TRPC4.

Also provided herein is a method of arresting podocytes from death comprising contacting the podocytes with a compound as disclosed herein. Further provided herein is a method of protecting podocytes from cytoskeletal disruption comprising contacting the podocytes with a compound as disclosed herein.

Also provided herein is a method of treating a subject suffering from kidney disease comprising administering a therapeutically effective amount of a compound as disclosed herein. In various cases, the kidney disease is proteinuric kidney disease, focal segmental glomerulosclerosis, minimal change disease, membranous glomerular nephropathy, membranoproliferative glomerulonephritis, C1q nephropathy, fibrillary glomerulonephritis, IgA nephropathy, anti-glomerular basement membrane disease, immune complex crescentic glomerulonephritis, Pauci-immune crescentic glomerulonephritis, or kidney failure. In various cases, the subject is human. In various cases, the subject exhibits decreased proteinuria upon administration of the compound.

Further provided herein is a method of treating a subject suffering from a TRPC5-mediated disease comprising administering to the subject a therapeutically effective amount of a compound as disclosed herein. In some cases, the TRPC5-mediated disease is a neuropsychiatric disorder, a neurodegenerative disorder, a nephropathy, or a seizure disorder.

AC1903 (30 µM) blocks ROS generation in vitro in caAT1R podocytes, similar to ML204 (30 µM) and the Rac1 inhibitor NSC23677 (50 µM). Veh n=(10 wells/experiment×4 independent replicates)=40 and 60, ML204 n=40 and 60, AC1903 n=40 and 60, NSC23677 n=40 and 60 for control and caAT1R expressing podocytes, respectively. Mean±SEM, *p<0.05. C) AC1903 (30 µM) prevents podocyte death in cells expressing caAT1R, similar to ML204 (30 µM) and the Rac1 inhibitor NSC23677 (50 µM). Control n=24, Vehicle n=24, ML204 n=24, AC1903 n=24, NSC23677 n=12. Mean±SEM, *p<0.05. D) AC1903 (50 mg/kg) ameliorates proteinuria in AT1R Tg rats with established, advanced disease. Veh n=13, AC1903 n=14, Mean±SEM, *p<0.05. E) AC1903 inhibition of TRPC5 channel activity in inside-out recordings from advanced disease AT1R rat glomeruli. AC1903 (1 µM) inhibits Rilu-activated (3 µM) conductance in glomeruli isolated from AT1R Tg rats with established disease. F) Quantification of open channel probability (NPo) for the conductances recorded in E. Blue bar, Riluzole measurement; Red bar, AC1903 measurement. n=6. Mean±SEM, *p<0.05. G) Toluidine blue semithin sections of rat kidneys. Red asterisks indicate pseudocysts. The pseudocyst volume observed in rat kidney sections is significantly reduced in AT1R Tg rats treated with AC1903. Size bar indicates 50 µM. H) Reduction of pseudocyst volume in AT1R Tg AC1903 rats compared to AT1R Tg vehicle rats. WT vehicle n=7, AT1R Tg vehicle n=7, AT1R Tg AC1903 n=7, Mean±SEM, *p<0.05. I) Rescue of podocyte numbers in vivo in AC1903-treated AT1R Tg rats with established disease (Advanced). WT vehicle n=7, AT1R Tg vehicle n=7, AT1R Tg AC1903 n=7, Advanced. Mean±SEM, *p<0.05.

Figure 5:
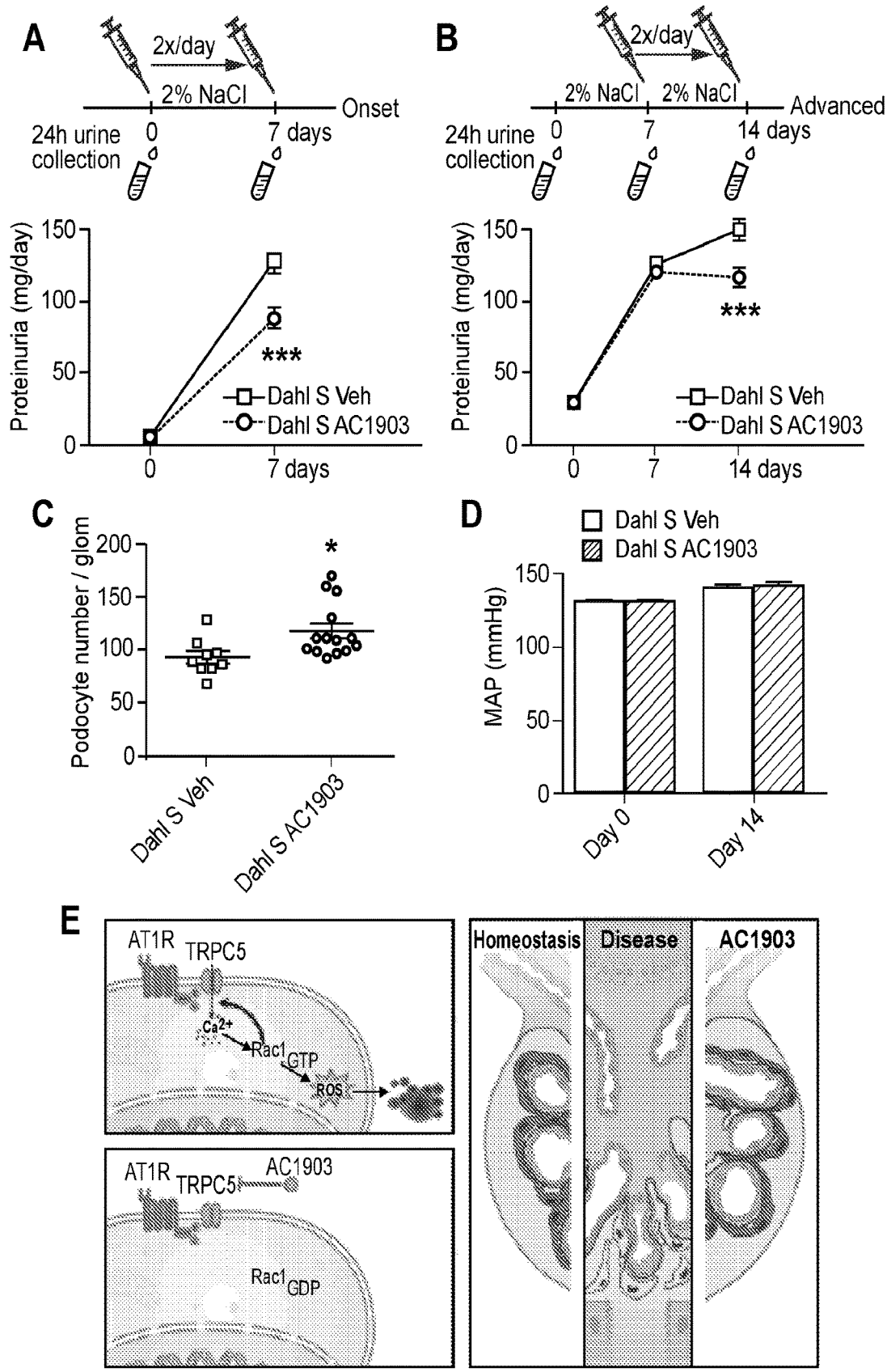

FIG. 5 shows AC1903 suppresses proteinuric kidney disease progression in Dahl S rats. A) AC1903 (50 mg/kg) ameliorates proteinuria in Dahl S rats when administered at the same time as high salt intake (Onset). Veh n=8, AC1903 n=8, Mean±SEM, *p<0.001. B) AC1903 (50 mg/kg) suppresses proteinuria in Dahl S rats with established, advanced disease (Advanced). Veh n=9, AC1903 n=11, Mean±SEM, *p<0.001. C) Rescue of podocyte numbers in vivo in AC1903-treated Dahl S rats with established disease (Advanced). Veh n=9, AC1903 n=11, Mean±SEM, *p<0.05. D) Administration of AC1903 has no effect on the mean arterial pressure (MAP) of Dahl S rats. E) Schematic model of the molecular mechanism of AC1903 at the cellular level (left), and the podocyte-protective effect of AC1903 treatment in vivo (right). On the left, Rac1 triggers TRPC5 activity as well as the generation of ROS. $Ca^{2+}$ influx through TRPC5 perpetuates the injury through further activation of Rac1 (upper). This disease pathway is disrupted by AC1903, which blocks TRPC5 channels, prevents ROS production and protects from podocyte loss (lower). On the right, during homeostasis, healthy podocytes (purple) are attached to the glomerular basement membrane through intact foot processes. In the setting of progressive disease, Rac1-TRPC5 signaling in podocytes (yellow) leads to podocyte loss, likely due to a combination of detachment from the basement membrane and/or cell death. Treatment with AC1903 prevents podocyte loss, indicating that TRPC5 inhibitors may be valuable for the treatment of progressive kidney diseases.

DETAILED DESCRIPTION

Provided herein are compounds that inhibit TRPC5, e.g., having a structure of Formula (I) or (II):

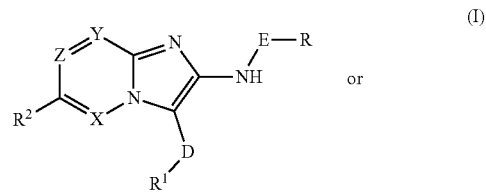

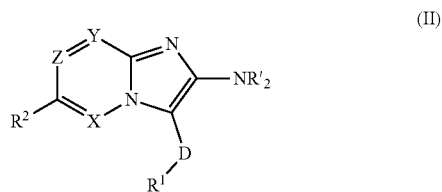

wherein X, Y, and Z are each independently N or $CR^2$; D is a bond, $C_1$-$C_4$alkylene, $C_0$-$C_4$alkylene-O—, or $C_0$-$C_4$alkylene-$NR^3$—; E is a bond, $C_1$-$C_4$alkylene, $C_1$-$C_4$alkylene-O—, $SO_2$, or C(O); R comprises $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O, and R is optionally substituted with one, two or three substituents selected from halo, CN, $C_1$-$C_6$alkyl, $C_1$-$C_6$haloalkyl, and $C_3$-$C_6$cycloalkyl; $R^1$ comprises $C_1$-$C_4$ alkyl, $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O, and $R^1$ is optionally substituted with one, two, or three substituents selected from halo, CN, $C_1$-$C_6$alkyl, $C_1$-$C_6$haloalkyl, and $C_3$-$C_6$cycloalkyl; each $R^2$ is independently H, halo, $C_1$-$C_5$alkyl, $C_1$-$C_5$haloalkyl, or $C_3$-$C_{12}$cycloalkyl; $R^3$ is H, $C_1$-$C_6$alkyl, $C_6$-$C_{12}$ aryl, or $C_3$-$C_{10}$ heteroaryl containing 1 to 3 ring heteroatoms selected from N, S, and O; and each R' together with the nitrogen atom to which they are attached form a 3-10 membered heterocycloalkyl containing 0 to 3 additional ring heteroatoms selected from N, S, and O, and the heterocycloalkyl is optionally substituted with one, two or three substituents selected from halo, CN, $C_1$-$C_6$alkyl, $C_1$-$C_6$haloalkyl, and $C_3$-$C_6$cycloalkyl. In some cases, the compound has a structure of Formula (IA), (IB), (10), or (ID):

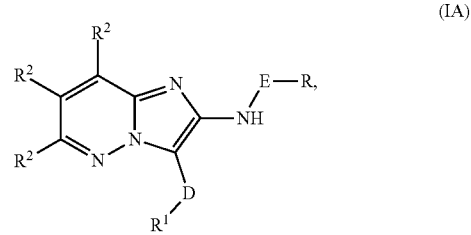

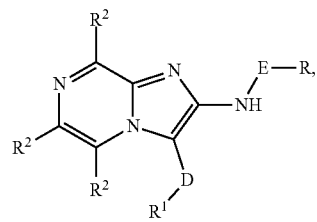
(IB)

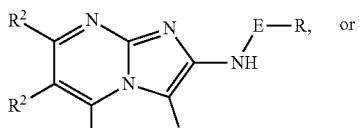
(IC)

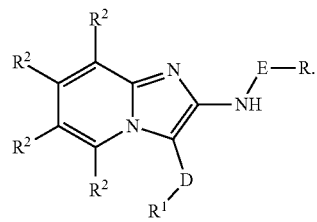
(ID)

In some cases, when the compound is a compound of Formula (ID), $R^1$ is $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O.

As used herein, the term "alkyl" refers to straight chained and branched saturated hydrocarbon groups. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. The term "haloalkyl" refers to an alkyl group substituted with at least one (e.g., 1 to 5) halo atom. Haloalkyl also includes alkyl groups that have all hydrogens replaced with halo atoms (e.g., $CF_3$).

The term "alkylene" used herein refers to an alkyl group having a substituent. For example, an alkylene group can be —$CH_2CH_2$— or —$CH_2$—. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

As used herein, the term "cycloalkyl" refers to an aliphatic cyclic hydrocarbon group that is monocyclic or polycyclic (e.g., bridged, fused, or spiro). The term $C_n$ means the cycloalkyl group has "n" carbon atoms. For example, $C_5$ cycloalkyl refers to a cycloalkyl group that has 5 carbon atoms in the ring. $C_3$-$C_6$ cycloalkyl refers to cycloalkyl groups having a number of carbon atoms encompassing the entire range (i.e., 3 to 6 carbon atoms), as well as all subgroups (e.g., 3-5, 4-6, 5-6, 3, 4, 5, and 6 carbon atoms). Nonlimiting examples of cycloalkyl groups include cyclopropyl, cyclobutyl, cyclopentyl, and cyclohexyl. Unless otherwise indicated, a cycloalkyl group can be an unsubstituted cycloalkyl group or a substituted cycloalkyl group.

As used herein, the term "heterocycloalkyl" refers to an aliphatic, non-aromatic monocyclic or polycyclic (e.g., bridged, fused, or spiro) group having 3-10 ring carbons and 1-3 ring heteroatoms selected from N, S, and O.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, $OCF_3$, $NO_2$, CN, NC, OH, alkoxy, amino, $CO_2H$, $CO_2$alkyl, aryl, and heteroaryl. Aryl groups can be isolated or fused to another aryl group, a cycloalkyl group, a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, "heteroaryl" refers to a monocyclic (e.g., 5 or 6 membered monocyclic ring having 3-5 carbon ring atoms) or polycyclic (e.g., 7-11 membered bicyclic ring having 5-10 carbon ring atoms) aromatic ring having 1, 2, or 3 heteroatoms selected from N, S, and O. In some embodiments, the heteroaryl ring comprises at least 1 ring nitrogen. Examples of contemplated heteroaryl groups include, but are not limited to, thienyl, furyl, pyridyl, pyrrolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. In some cases, the heteroaryl can be pyrrolyl, pyrazolyl, imidazolyl, triazolyl, pyridyl, pyrazinyl, pyrimidinyl, indolyl, indazolyl, benzotriazolyl, benzoimidazolyl, pyrrolopyridinyl, or imidazopyrindinyl. In various cases, the heteroaryl can be pyridyl, pyrimidinyl, pyrrolopyridinyl, indazolyl, or imidazopyrindinyl.

The term "halo" refers to fluoro, chloro, bromo, and iodo.

Some specific compounds contemplated are compounds having a structure:

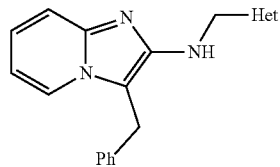

where the Het group comprises furyl, thienyl, thiazolyl, oxazolyl, oxadiazolyl, thiadiazolyl, pyridyl, pyridazinyl, pyrimidinyl, pyrazinyl, pyranyl, tetrahydrofuryl, tetrahydropyranyl, morpholinyl, piperadinyl, thiomorpholinyl, or piperazinyl. In some cases, the $CH_2$Het group is selected from

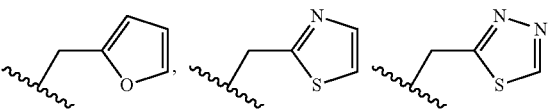

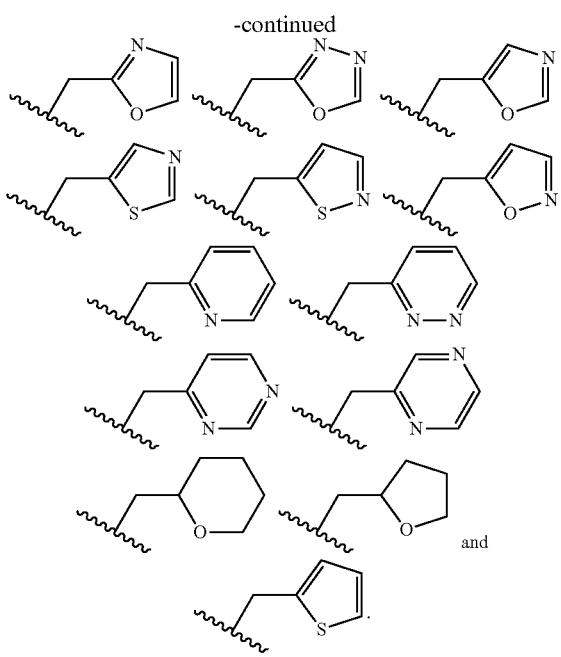

The 'CH₂Ph' noted in the above structure can alternatively be $C_{1-2}$alkylene-O-Ph or $C_{1-2}$alkylene-Het (where Het is a group noted as above). The "Ph" or "Het" can be substituted, e.g., with one or more moieties such as halo (e.g., F or Cl), CN, $C_1$-$C_6$alkyl (e.g., Me or Et), $C_1$-$C_6$haloalkyl (e.g., $CF_3$), and $C_3$-$C_6$cycloalkyl. Thus, while the Het groups explicitly shown drawn above do not show substitution, it is explicitly contemplated that any one of these Het groups can be substituted with one of these moieties.

In various cases, each $R^2$ is H. In some cases, at least one $R^2$ is halo.

In various cases, D is a bond. In other cases, D is $C_1$-$C_4$alkylene, $C_0$-$C_4$alkylene-O—, or $C_0$-$C_4$alkylene-$NR^3$. D can be $CH_2$ or $CH_2CH_2$, or can be $CH_2CH_2O$.

In various cases, E is $C_1$-$C_4$alkylene or $C_1$-$C_4$alkylene-O. In some cases, E is $CH_2$. In some cases, E is a bond. In some cases, E is C(O) or $SO_2$.

In various cases, R comprises $C_3$-$C_{10}$ heteroaryl containing 1 to 3 ring heteroatoms selected from N, S, and O or $C_3$-$C_{10}$ heterocycloalkyl containing 1 to 3 ring heteroatoms selected from N, S, and O. In some cases, R comprises $C_3$-$C_{10}$ heteroaryl containing 1 to 3 ring heteroatoms selected from N, S, and O. R can comprise furyl, thienyl, thiazolyl, oxazolyl, oxadiazolyl, thiadiazolyl, pyridyl, pyridazinyl, pyrimidinyl, pyrazinyl, pyranyl, tetrahydrofuryl, or tetrahydropyranyl. R can comprise phenyl.

In some cases, the compound is a compound of Formula (II). In some embodiments of these cases, —NR'₂ forms a 5-6 membered heterocycloalkyl ring having 0-1 additional ring heteroatoms selected from N, O, and S. In some cases, the —NR'₂ heterocycloalkyl ring is substituted with one, two or three substituents selected from halo, CN, $C_1$-$C_6$alkyl, $C_1$-$C_6$haloalkyl, and $C_3$-$C_6$cycloalkyl. In some cases, the —NR'₂ heterocycloalkyl ring is unsubstituted.

In various cases, $R^1$ comprises phenyl. In various cases, $R^1$ comprises $C_3$-$C_{10}$ heteroaryl containing 1 to 3 ring heteroatoms selected from N, S, and O or $C_3$-$C_{10}$ heterocycloalkyl containing 1 to 3 ring heteroatoms selected from N, S, and O. $R^1$ can comprise furyl, thienyl, thiazolyl, oxazolyl, oxadiazolyl, thiadiazolyl, pyridyl, pyridazinyl, pyrimidinyl, pyrazinyl, pyranyl, tetrahydrofuryl, tetrahydropyranyl, morpholinyl, piperadinyl, thiomorpholinyl, or piperazinyl. $R^1$ can comprise $C_1$-$C_4$ alkyl.

Specifically contemplated compounds include those as listed in Table 1.

TABLE 1

| | Structure |
|---|---|
| 1 | 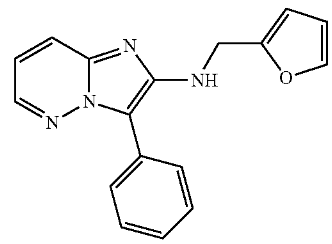 [SMILES: c1ccc(-c2c(NCc3ccco3)nc3cccnn23)cc1] |
| 2 | 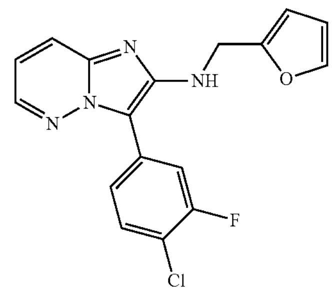 [SMILES: Fc1cc(-c2c(NCc3ccco3)nc3cccnn23)ccc1Cl] |
| 3 | 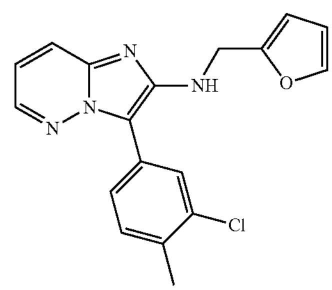 [SMILES: Cc1ccc(-c2c(NCc3ccco3)nc3cccnn23)cc1Cl] |
| 4 | 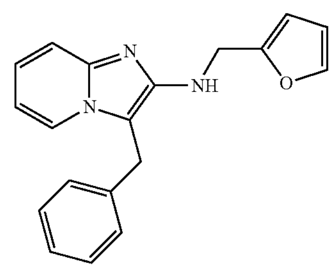 [SMILES: c1ccc(Cc2c(NCc3ccco3)nc3ccccn23)cc1] |
| 5 | 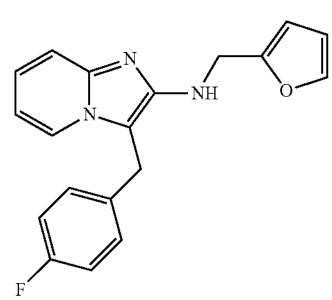 [SMILES: Fc1ccc(Cc2c(NCc3ccco3)nc3ccccn23)cc1] |

TABLE 1-continued

Structure

6. [Structure: imidazo[1,2-a]pyridine with 3-benzyl and 2-(pyridin-3-ylamino) substituents]

7. [Structure: imidazo[1,2-b]pyridazine with benzyl and pyrrolidinyl substituents]

Pharmaceutical Formulations and Administration

The methods provided herein include the manufacture and use of pharmaceutical compositions, which include one or more of the compounds provided herein. Also included are the pharmaceutical compositions themselves. Pharmaceutical compositions typically include a pharmaceutically acceptable carrier. Thus, provided herein are pharmaceutical formulations that include a compound described herein and one or more pharmaceutically acceptable carriers.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some embodiments, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety.

As described above, the preparations of one or more compounds provided herein may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

A compound provided herein may be administered to humans and other animals for therapy by any suitable route of administration, including orally, nasally, as by, for example, a spray, rectally, intravaginally, parenterally, intracistemally, and topically, as by powders, ointments or drops, including buccally and sublingually. Regardless of the route of administration selected, a compound provided herein, which may be used in a suitable hydrated form, and/or the pharmaceutical compositions provided herein, is formulated into a pharmaceutically acceptable dosage form by conventional methods known to those of skill in the art. In another embodiment, the pharmaceutical composition is an oral solution or a parenteral solution. Another embodiment is a freeze-dried preparation that can be reconstituted prior to administration. As a solid, this formulation may also include tablets, capsules or powders.

Actual dosage levels of the active ingredients in the pharmaceutical compositions provided herein may be varied so as to obtain "therapeutically effective amount," which is an amount of the active ingredient effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is also noted that the dose of the compound can be varied over time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The pharmaceutical compositions can be included in a container, pack, or dispenser together with instructions for administration.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

TRPC5 Inhibition

Cation channels such as TRPC5 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Transient receptor potential (TRP) homomeric TRPC5 ion channels are signal transduction gated, $Ca^{2+}$-permeable channels predominantly expressed in the neurons. TRPC5 forms homomultimeric structures such as tetramers (i.e., TRPC5 homomultimers) and heteromultimeric structures such as tetramers (i.e., TRPC5-TRPC1 heteromultimers).

Modulating the function of TRPC5 provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

In various cases, the compounds disclosed herein selectively inhibit TRPC5, compared to TRPC4 and/or TRPC6. Selective inhibition means that the compound inhibits TRPC5 to a greater extent that TRPC4 and/or TRPC6. For example, the selectivity of a compound can be represented a number, where 1 indicates no selectivity for either target, and a number greater than 1 indicates a selectivity for TRPC5, while a number less than 1 indicates a selectivity for TRPC4. The selectivity of a compound for TRPC5 compared to TRPC6 can be represented a number, where 1 indicates no selectivity for either target, and a number greater than 1 indicates a selectivity for TRPC5, while a number less than 1 indicates a selectivity for TRPC6. In some cases, the selectivity for TRPC5 of a compound disclosed herein is at least 2, at least 3, at least 4, at least 5, at least 6, at least 7, at least 8, at least 9, or at least 10, compared to TRPC4 or TRPC6. Thus, a compound as disclosed herein can have two selectivity properties—one for selectivity of TRPC5 compared to 4 and one for TRPC5 compared to TRPC6. Inhibition of TRPC4, TRPC5, and TRPC6 can be assessed using an assay known in the art, and/or as described in the Examples below.

Methods of Using TRPC5 Inhibitors

Inhibition of TRPC5 is implicated in a number of biological pathways, including Rac1 signaling in podocytes. Thus, provided herein are methods of arresting podocytes from death and/or protecting podocytes from cytoskeletal disruption by contacting the podocytes with a compound as disclosed herein.

Also provided are methods of treating a subject suffering from a TRPC-mediated disease. Non-limiting examples include kidney disease, a neuropsychiatric disorder, a neurodegenerative disorder, a nephropathy, or a seizure disorder.

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging. Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72: 1061-1068; Leissring et al. (1999) J. Biol. Chem. 274 (46):32535-32538; Leissring et al. (2000) J. Cell Biol. 149 (4):793-797; Leissring et al. (2000) Proc. Natl. Acad. Sci. U.S.A. 97 (15): 8590-8593). Furthermore, mutations in PS1 or PS2 associated with an increase in amyloidogenic amyloid β peptide generation in AD are reported to be associated with a decrease in intracellular calcium level (Yoo et al. (2000) Neuron, 27 (3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17 (1):83-91).

Seizure: Excitotoxicity of a variety of origins leads to seizures. Commonly excess neuronal firing can drive seizure activity. Compounds that reduce the hyperexcitability of relevant neuronal populations have significant potential in reducing seizure activity.

Kidney Disease: TRPC5 is also expressed in the podocyte of the kidney. It has been proposed that there is an antagonistic regulation of actin dynamics and cell motility in podocytes by TRPC5 and TRPC6 (Tian et al., (2010) Science Signaling). Thus, inhibiting TRPC5 may impact the reaction of the podocyte to injury. The kidney disease can be proteinuric kidney disease, focal segmental glomerulosclerosis, minimal change disease, membranous nephropathy, membranoproliferative glomerulonephritis, C1q nephropathy, fibrillary glomerulonephritis, IgA nephropathy, anti-glomerular basement membrane disease, immune complex crescentic glomerulonephritis, Pauci-immune crescentic glomerulonephritis, or kidney failure. In various cases, the subject exhibits decreased proteinuria upon administration of the compound as disclosed herein.

Research Studies

To study the role of Rac1-TRPC5-mediated podocyte injury in FSGS, AT1R transgenic (TGNeph-hAT1R/185 or AT1R Tg) rats were used, which express the human AT1R in a podocyte-specific manner (13). These rats develop progressive proteinuria, increased abundance of Rac1 in podocytes, histologic evidence of FSGS and die of kidney failure by 60 weeks of life (13, 14). Similar to FSGS patients (3), these rats develop all the classical features of nephrotic syndrome, including high circulating lipids and low serum albumin, thus serving as a relevant preclinical model system in which to study FSGS progression (13). Because they have podocyte-specific expression of the AT1R, these animals do not experience any of the systemic effects of excess angiotensin signaling, such as hypertension or vascular disease (13), thus allowing for a focus on podocyte-specific pathology.

Figure 1:
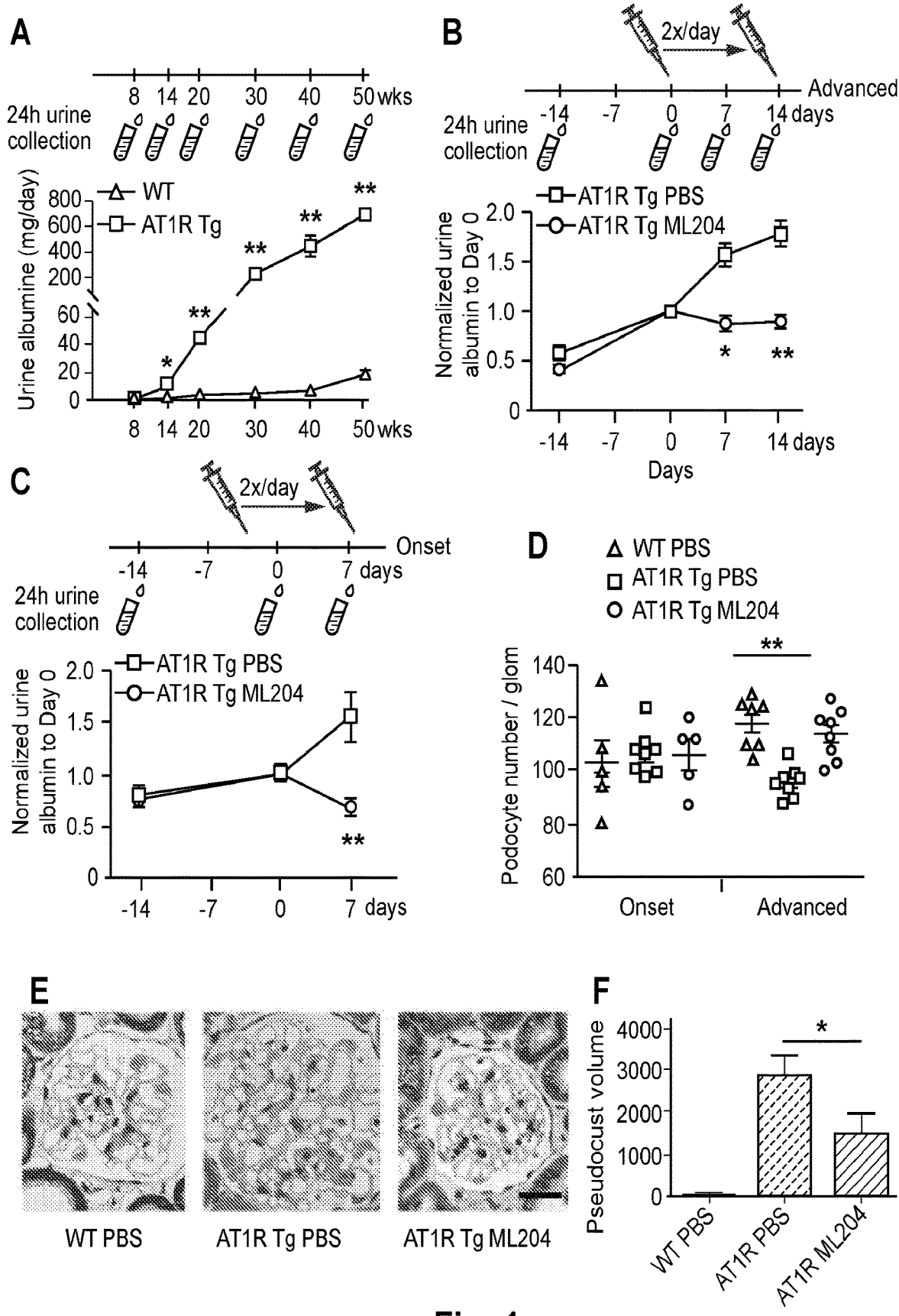
FIG. 1 shows TRPC5 inhibition prevents podocyte loss in AT1R Tg rats with severe, progressive FSGS. A) Severe, progressive proteinuria in AT1R Tg rats over the course of 50 weeks, with onset of disease at >8 weeks and severe escalation in proteinuria starting at 14 weeks. WT n=91, AT1R Tg n=122, Mean±SEM, *p<0.05, **p<0.01. B) Twice per day (2×/day) i.p. administration of ML204 suppresses progressive proteinuria in the Advanced cohort of AT1R Tg rats treated for 14 days. AT1R Tg PBS n=23, AT1R Tg ML204 n=23, Mean±SEM, *p<0.05, p<0.01. C) Twice per day (2×/day) i.p. administration of ML204 at disease onset blocks proteinuria to complete remission. WT PBS n=5, AT1R Tg PBS n=8, AT1R Tg ML204 n=5, Mean±SEM, p<0.01. D) Rescue of podocyte numbers in vivo in ML204-treated AT1R Tg rats with established disease (Advanced). WT PBS n=5 and 7, AT1R Tg PBS n=8 and 8, AT1R Tg ML204 n=5 and 8 for Onset and Advanced groups, respectively. Mean±SEM, **p<0.01. E) Toluidine blue semithin sections of rat kidneys. Red asterisks indicate podocyte pseudocysts. This is observed in AT1R Tg rat sections, but not in AT1R Tg rats treated with ML204, similar to WT controls. Size bar indicates 50 µM. F) Reduction of pseudocyst volume in AT1R Tg ML204 rats compared to AT1R Tg PBS rats. WT PBS n=7, AT1R Tg PBS n=9, AT1R Tg ML204 n=8, Mean±SEM, *p<0.05.

AT1R Tg rats developed severe, progressive proteinuria over the course of 50 weeks, with onset of disease at 8-14 weeks and severe escalation in proteinuria beyond 14 weeks (FIG. 1A). As a consequence of their progressive kidney failure, AT1R Tg rats died by approximately 500 days of life, significantly earlier than wild-type (WT) controls. To understand the role of TRPC5 signaling in FSGS disease progression, AT1R Tg rats with established, advanced disease (Advanced), defined by severe proteinuria, were assessed and compared to younger rats, experiencing the onset of disease (Onset).

ML204, a published tool compound that blocks TRPC5 (15), was selected for in vivo therapeutic studies. The compound also blocks TRPC4 channels (1:1 to TRPC5) and may also weakly block TRPC6 channels (1:20 to TRPC5) (15). Testing ML204 in rats with advanced disease, similar to FSGS patients who present with severe, nephrotic range proteinuria, was of interest (3). Remarkably, the administration of ML204 (25 mg/kg) twice daily over the course of 14 days in rats with severe, advanced disease (Advanced) suppressed progression of proteinuric disease at 7 days and 14 days, while control animals continued to experience disease escalation (FIG. 1B). ML204 administered over 7 days was sufficient to suppress disease progression (FIG. 1B). At disease onset (Onset), ML204 was administered twice daily for 7 days (FIG. 1C). This resulted in complete suppression of proteinuria down to baseline levels (FIG. 1C), indistinguishable from WT controls.

Detailed morphometric analysis (a state of the art approach validated for both rodent and human tissue (16, 17); see Methods) of ML204 treated animals compared to controls was performed, to explain the sustained therapeutic effect, even in the case of severe and progressive disease. Measurements revealed that ML204 prevented podocyte loss in Tg rats with advanced disease, maintaining the numbers of podocytes at near-baseline WT levels, in contrast to significant podocyte loss in control PBS-treated Tg rats (FIG. 1D). Morphometric analysis demonstrated podocyte pseudocyst formation in AT1R Tg rats with advanced disease (FIG. 1E), similar to previously described cases of pseudocysts leading to podocyte loss through detachment in various models of FSGS (18). Treatment with ML204 prevented pseudocyst formation, suggesting that podocytes were rescued from detachment and loss (FIG. 1E, F). AT1R Tg rats did not have elevated blood urea nitrogen (BUN) and creatinine levels during this experiment, similar to many patients with nephrotic range proteinuria due to FSGS (3). Treatment with ML204 did not affect body weight, BUN or creatinine. Thus, podocyte numbers are preserved by treatment with ML204. These experiments offered the first hint of a podocyte-protective therapeutic strategy targeted to TRPC5 channels.

To study the contribution of specific TRPC channels to the podocyte-preserving effects of ML204 in vivo, $Ca^{2+}$ imaging experiments were performed to record podocyte $Ca^{2+}$ transients in situ in intact isolated glomeruli (11). Trivalent $La^{3+}$ was used, which blocks all TRPC channels with the exception of TRPC5, which it potentiates (10). $La^{3+}$ reduced the Angiotensin II (AngII)-mediated podocyte $Ca^{2+}$ response in glomeruli from WT rats. In contrast, Ang-II mediated $Ca^{2+}$ influx was resistant to block by $La^{3+}$ during disease onset (Onset), and was overtly increased in Tg rats with established disease (Advanced). These data, together with previously established TRPC6 and TRPC5 native conductances in podocytes (10), suggested that the $La^{3+}$-sensitive TRPC6 plays a homeostatic role in WT intact glomeruli, but TRPC5, unmasked by $La^{3+}$, shows increased activity at the onset of proteinuria (Onset) and predominates during advanced disease progression (Advanced).

Figure 2:
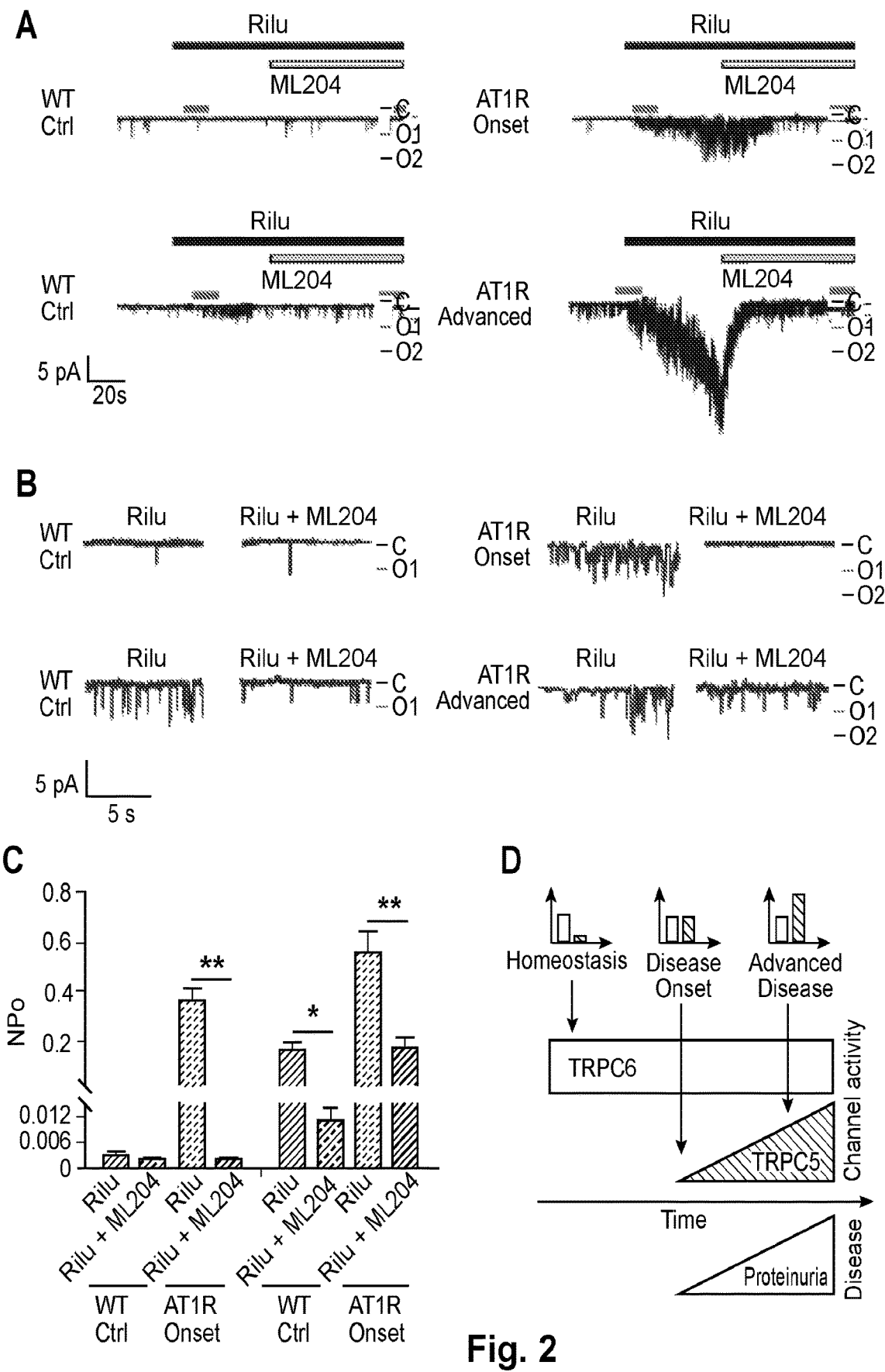
FIG. 2 shows TRPC5-mediated single channel activity increases with FSGS disease progression. A) ML204 (1 µM) blocks TRPC5 channel activity induced by Riluzole (Rilu, 3 µM) in inside-out recordings from rat glomeruli isolated at disease onset (Onset), as compared to barely detectable current in age matched WT rat glomeruli (Onset). ML204 blocks a significantly greater Rilu-activated conductance in glomeruli isolated from rats with established disease (Advanced), compared to minimal TRPC5 activity in age matched WT glomeruli (Advanced). C, close state, $O_1$, open channel level 1, $O_2$, open channel level 2. $V_m$=−60 mV. B) Magnified single-channel recording traces before and after ML204. Colored bars in A correspond to colored traces (blue, red) below. C) Quantification of open channel probability (NPo) for the conductances recorded in A. ML204 blocks Rilu-induced conductances in isolated AT1R Tg glomeruli from onset of disease (Onset) and after established disease (Advanced). WT Rilu n=4 and 5, WT Rilu+ML204 n=4 and 5, AT1R Tg Rilu n=4 and 5, AT1R Tg Rilu+ML204 n=4 and 5 for Onset and Advanced groups, respectively. Mean±SEM, *p<0.05, **p<0.01. D) TRPC6 channel activity contributes to podocyte $Ca^{2+}$ homeostasis. TRPC5 activity is coincident with onset of proteinuria and correlates with FSGS disease progression.

Patch clamp electrophysiology adapted to the intact isolated glomeruli preparation was investigated. Riluzole (19) was used as a direct activator of TRPC5 channel activity. In inside-out recordings of podocytes from AT1R Tg rat glomeruli isolated at disease onset (Onset), significant ML204 inhibition of channel activity was recorded. ML204 inhibition of a much greater riluzole-activated conductance was noted in glomeruli from rats with established disease (Advanced) (FIG. 2A, B). In contrast, minimal riluzole-mediated TRPC5 activation in WT rat glomeruli in age-matched controls was recorded (FIG. 2A-C). To examine effects on TRPC6 channels, 1-oleoyl-2-acetyl-glycerol (OAG) was used, which directly activates these channels (20). Importantly, no inhibition of ML204 on OAG-induced conductances in recordings from age matched AT1R Tg rats and WT controls. The possibility that the therapeutic effect of ML204 can be explained by its targeting of TRPC6 channel activity in AT1R Tg rats at any stage of disease progression was therefore excluded. In addition, the effects of ML204 in podocytes cannot be explained by inhibition of TRPC4, inasmuch as this channel is not expressed in these cells (10). The conclusion from these ex vivo $Ca^{2+}$ imaging and electrophysiological studies is that TRPC5-mediated $Ca^{2+}$ influx in podocytes correlates with FSGS disease progression (FIG. 2D), which is suppressed by ML204.

Figure 3:
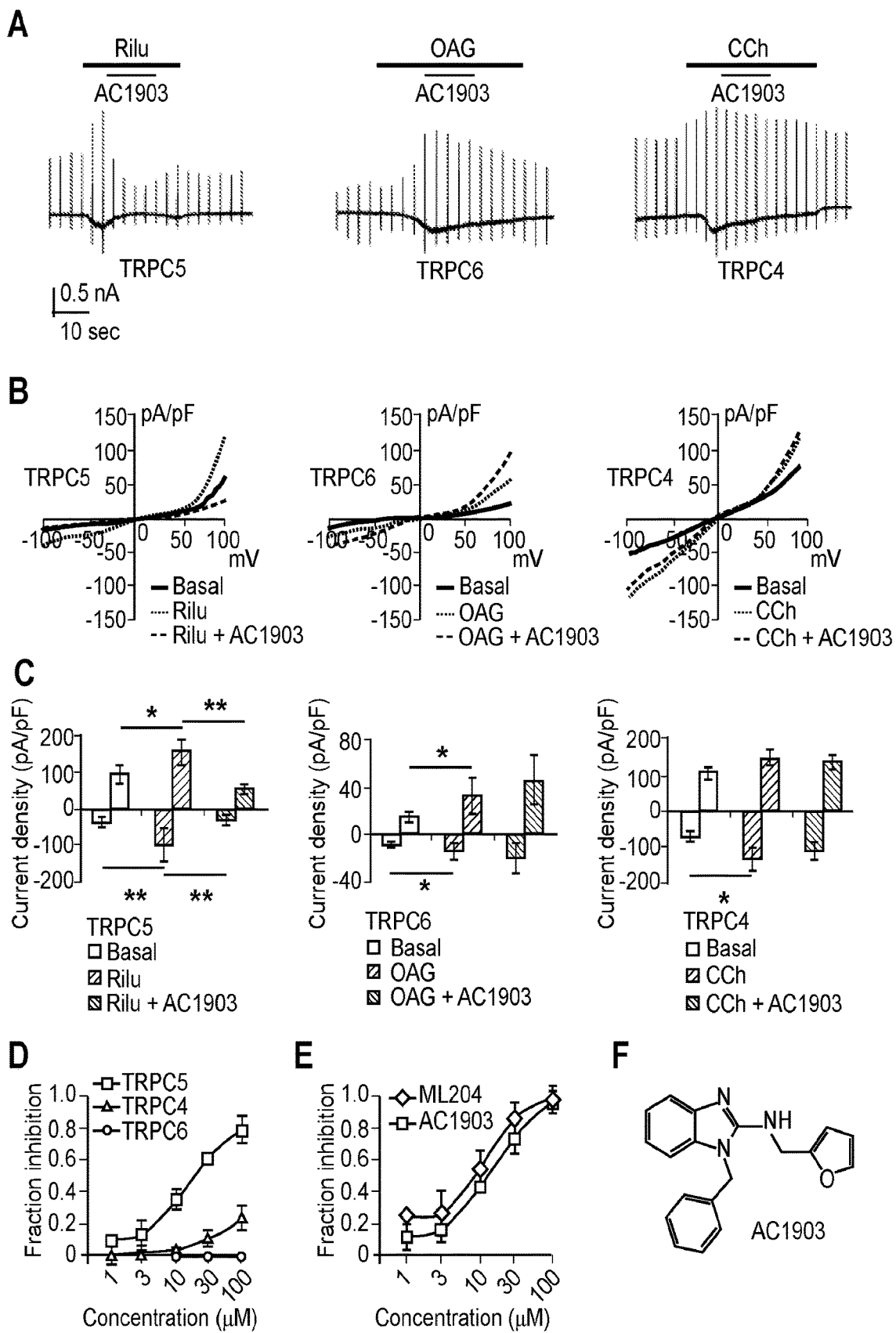
FIG. 3 shows AC1903 is a specific TRPC5 small molecule inhibitor. A) Representative whole-cell current recordings of AC1903 effects on TRPC5, TRPC6 and TRPC4 channels. AC1903 (30 µM) blocks Rilu-activated TRPC5 whole cell conductance in HEK cells expressing TRPC5. No AC1903 effect on OAG-activated (30 µM) TRPC6 channel activity or CCh-activated (100 µM) TRPC4 channel activity. B) Representative current-voltage (I-V) relationships show that AC1903 specifically inhibits TRPC5 channel activity versus TRPC6 and TRPC4 channel activity. Current density in pA/pF. C) Quantification of whole cell recordings. AC1903 specifically inhibits TRPC5-mediated inward and outward current, but does not inhibit TRPC6 or TRPC4 currents. Current density in pA/pF. TRPC5 n=6, TRPC6 n=6, TRPC4 n=5. Mean±SEM, *p<0.05, **p<0.01. D) Dose response (1-100 µM) for AC1903-mediated inhibition of TRPC5 channels compared to TRPC4 and TRPC6 channels demonstrates selectivity of AC1903 for TRPC5. n>3 for each dose. Mean±SEM. E) Equipotency between AC1903 and ML204 in dose response patch clamp experiments in the whole cell configuration in response to Rilu (3 µM). ML204 n>3, AC1903 n>3 for each dose. Mean±SEM. F) Chemical structure of AC1903.

ML204 blocks TRPC4 and TRPC5 channels, and also has weak effects on TRPC6 channels (15). A compound with podocyte-protective properties and no unwanted on-target effects on TRPC4 channels (which, although not expressed in podocytes (10), are expressed in endothelium (21)) or TRPC6 channels was desired. Based on the structures of published blockers (15, 22), medicinal chemistry efforts to synthesize and test a series of 50 molecules for activity against TRPC4, TRPC5 and TRPC6 was undertaken. These efforts ultimately yielded the compound AC1903 (FIG. 3). AC1903 was evaluated in patch-clamp electrophysiology experiments in HEK cells expressing TRPC5, and compared it to cells expressing TRPC4 and TRPC6. These experiments showed that AC1903 is TRPC5-selective: it blocked riluzole-activated TRPC5 whole-cell current, but failed to block carbachol (CCh)-induced TRPC4 and OAG-induced TRPC6 currents, even at a high concentration (30 µM) (FIG. 3A, B). The selectivity of AC1903 for TRPC5 was confirmed in dose-response experiments in HEK cells expressing TRPC5, TRPC4 or TRPC6 (FIG. 3D). The dose responses of AC1903 and ML204 were compared, and the two inhibitors were nearly equipotent, with $IC_{50\ ML204}$ 13.6 µM versus $IC_{50\ AC1903}$ 14.7 µM (FIG. 3E). In standard kinase profiling assays, AC1903 was not found to have any off-target effects. These experiments provided evidence that AC1903 (FIG. 3F) is a specific TRPC5 ion channel blocker.

Figure 4:
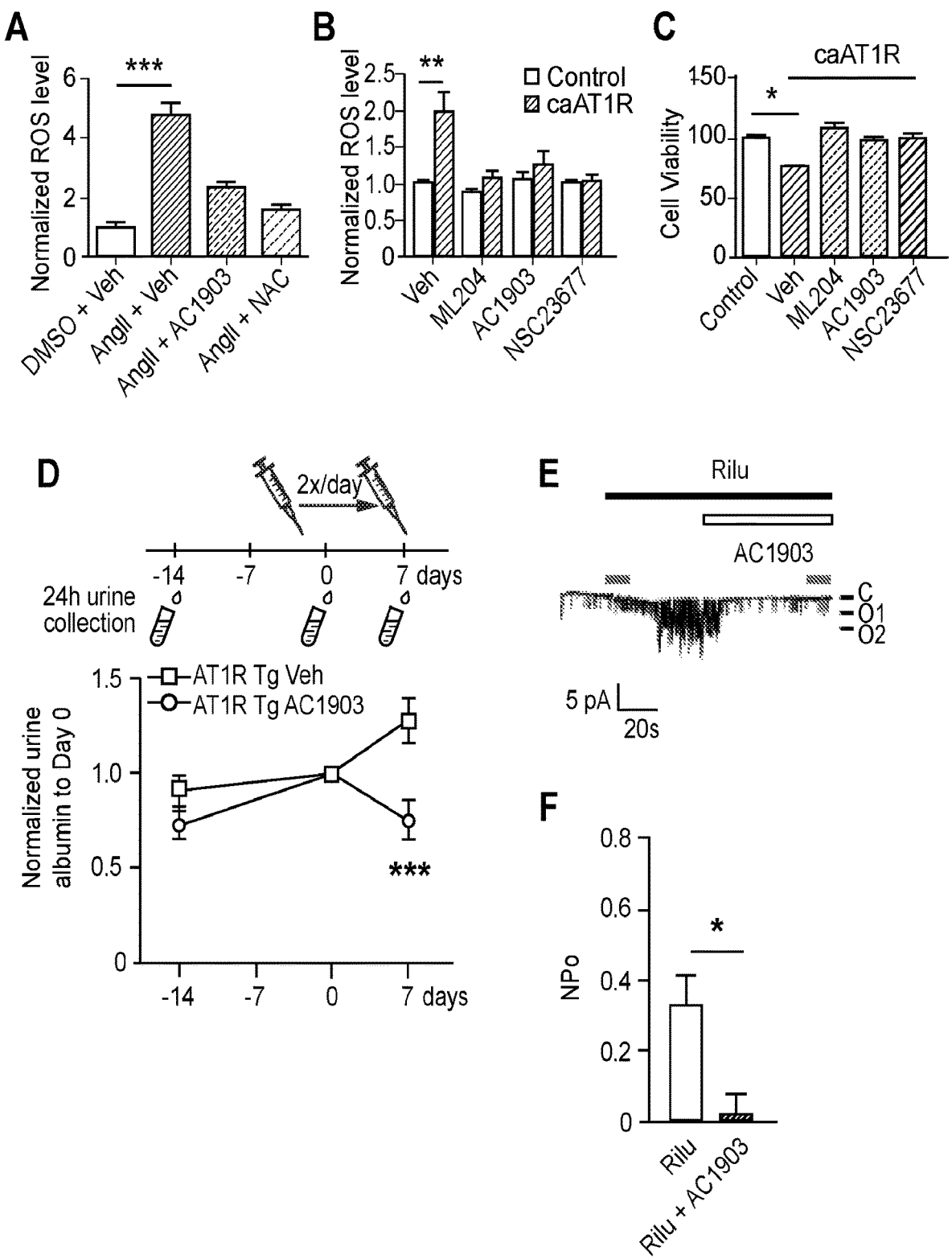
FIG. 4 shows AC1903 suppresses proteinuric kidney disease progression in AT1R Tg rats with advanced disease. A) AC1903 (30 µM) blocks ROS generation in vitro in wild-type podocytes treated with AngII (10 µM), similar to the ROS scavenger N-acetyl-L-cysteine (NAC, 30 µM). DMSO+Veh n=23, Ang II+Veh n=23, Ang II+AC1903 n=24, Ang II+NAC n=24. Mean±SEM, ***p<0.001. B)
Figure 4:
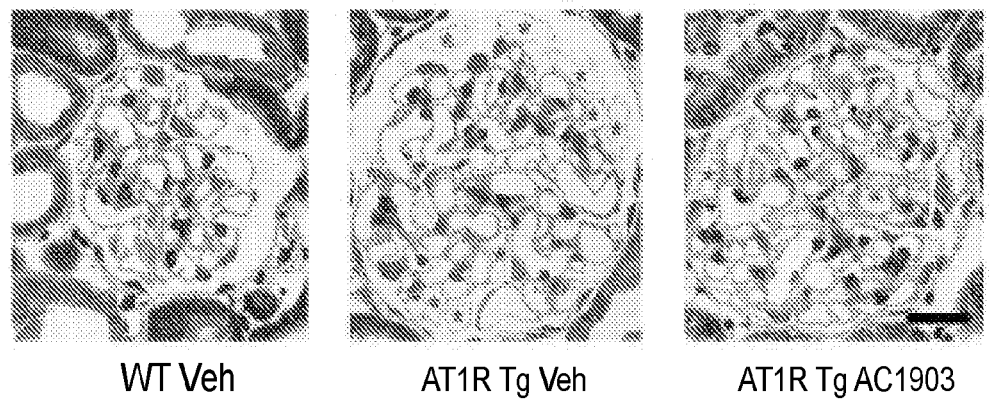
Figure 4:
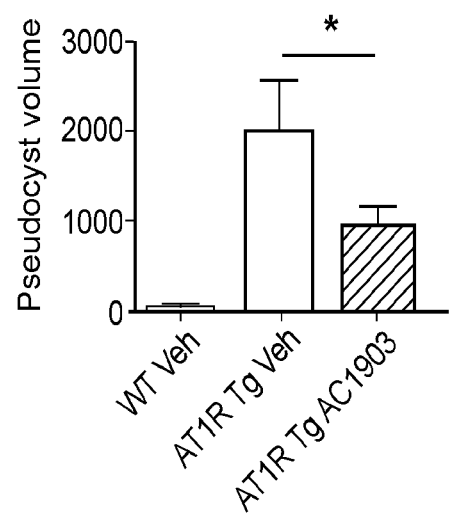
Figure 4:
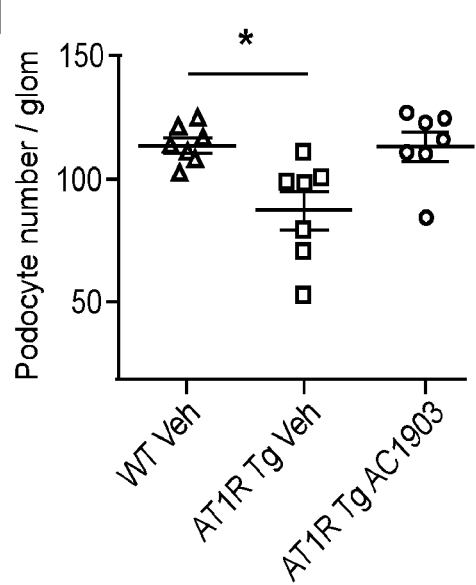

To establish a mechanistic understanding for the effects of AC1903 on the Rac1-TRPC5 pathway in podocytes, reactive oxygen species (ROS) were measured in vitro, because Rac1 activation leads to increased ROS production (23, 24). ROS was measured in WT podocytes treated with AngII (FIG. 4A). AngII treatment induced a significant increase in ROS, which was blocked by AC1903 and the ROS scavenger N-acetylcysteine (NAC) rescued podocytes from AngII-induced ROS (FIG. 4A). In an complementary study, an in vitro model was designed to mirror AT1R-expressing podocytes in Tg rats. Here podocytes were engineered to overexpress a well-characterized, constitutively active mutant of the human AT1R, which is unable to inactivate and undergo endocytosis (constitutively active AT1R or caAT1R) (25). Increased ROS production was detected in the presence of caAT1R (FIG. 4B). AC1903, ML204 and the Rac1 inhibitor (NSC23677) blocked caAT1R-induced ROS generation (FIG. 4B). Podocytes also showed increased cell death within 36 hours of caAT1R expression (FIG. 4C). In contrast, podocytes treated with AC1903, ML204 or the Rac1 inhibitor were protected from cell death (FIG. 4C). These data suggest that excess ROS production contributes to the molecular events linking Rac1-TRPC5 signaling to podocyte loss.

To enable in vivo studies, the pharmacokinetic properties of AC1903 were characterized, suggesting an AC1903 dose of 50 mg/kg was appropriate for these studies. Whether AC1903 can suppress proteinuria in AT1R Tg rats with established, severe disease was investigated. Twice daily i.p. injections of AC1903 for 7 days were sufficient to suppress severe proteinuria in AT1R Tg rats (Advanced)(FIG. 4C). Inside-out electrophysiology measurements in intact glomeruli from AT1R Tg rats confirmed that AC1903 blocks TRPC5 channel activity during proteinuric disease progression (FIG. 4D, E). Morphometric analysis demonstrated a significant reduction in pseudocyst formation in AT1R Tg rats with advanced disease treated with AC1903 (FIG. 4F, G)(18). AT1R Tg rats treated with AC1903 also had preserved numbers of podocytes compared to vehicle treated controls, in support of the notion that preventing pseudocysts also prevents podocyte loss (FIG. 4H). Treatment with AC1903 did not affect the BUN and creatinine or the body weight of rats in this experiment. These data show for the first time that a specific TRPC5 inhibitor can suppress proteinuric kidney disease progression by preserving the precious pool of podocytes.

To characterize the transcriptional responses to AC1903-mediated inhibition of Rac1-TRPC5 signaling and enhanced podocyte survival in vivo, gene expression profiles (RNASeq) in isolated glomeruli from WT rats, AC1903-treated AT1R Tg rats in the advanced cohort and vehicle-treated, age-matched AT1R Tg controls were compared. There were 541 differentially expressed genes in AT1R Tg rats compared to WT controls. Interestingly, Gene Ontology (GO) term enrichment analysis revealed ROS-related and ion (cation) channel and transporter activity gene signatures, in line with the hypothesis that Rac1-mediated ROS generation and TRPC5 $Ca^{2+}$ (cation) mediated signaling lead to disease progression. Consistent with this, ROS-related genes previously implicated in podocyte injury such as Nox4 (26, 27) were found to be upregulated, whereas genes whose loss of function in patients is associated with FSGS, such as EMP2(28) and KANK1(29), were downregulated in AT1R Tg rats. After treatment with AC1903, 42 genes were differentially expressed in AC1903-treated versus vehicle-treated AT1R Tg rats. This smaller number of genes suggests that AC1903 targets a specific signaling network to confer its therapeutic benefit. GO term enrichment analysis revealed cell adhesion and integrin signaling gene sets, in support of the notion that AC1903 fortifies the cytoskeleton and promotes cell adhesion to prevent podocytes loss. In short, the in vivo gene expression profiles support a Rac1-TRPC5 disease-promoting pathway in proteinuric kidney disease that is reversed by treatment with AC1903 to promote podocyte survival.

The Dahl salt-sensitive (Dahl S) rat is a commonly used model to study hypertension-induced FSGS (30, 31). Dahl S rats exhibit progressive kidney injury related to age with moderate hypertension when raised on a low-salt diet, and they demonstrate progressive nephrotic range proteinuria and decline in kidney function with significant hypertension when raised on a high-salt diet (32). Dahl S rats develop proteinuria and hypertension mediated at least in part by AngII (30, 31, 33), so this preclinical model was selected to extend and validate the work in AT1R Tg rats. The efficacy of AC1903 was tested in hypertensive Dahl S rats with salt-loading (2% NaCl) in comparison to vehicle-treated rats. First, AC1903 was injected (50 mg/kg twice daily i.p.) into 6 week old Dahl S rats at the same time as the start of 2% NaCl diet (Onset, FIG. 5A). As expected, control rats developed severe and escalating proteinuria within a week of salt administration (FIG. 5A). In contrast, the rate of progressive proteinuria in AC1903-treated animals was significantly reduced (FIG. 5A). Next, 6 week old Dahl S rats received 2% NaCl for one week, leading to severe, progressive proteinuric disease (advanced, FIG. 5B). AC1903 treatment was initiated on day 7, and animals were treated for 1 week until day 14 (2 weeks salt-loading). While progressive proteinuria continued to escalate in control rats, AC1903-treated rats had significant suppression of proteinuria (FIG. 5B) which was associated with a preservation of podocyte numbers. Morphometric analysis showed that the numbers of podocytes per glomerulus in AC1903 treated Dahl S rats was higher compared to vehicle-treated controls, and similar to the numbers of podocytes in WT and AC1903-treated AT1R Tg rats (approximately 120 podocytes/glom, FIG. 1D; FIG. 4H; FIG. 5C). AC1903 had no effect on body weight, BUN or creatinine in Dahl S rats in these experiments. Importantly, treatment with AC1903 did not affect the mean arterial pressure (MAP), suggesting that the therapeutic benefit is not related to changes in blood pressure, and therefore more likely due to direct podocyte protective effect (FIG. 5D).

In summary, these data demonstrate that a small molecule inhibitor of TRPC5 channels administered after established, advanced proteinuric disease can rescue podocytes and suppress the progression of morphologic and molecular changes that characterize this disease. In rats with systemic hypertensive disease, AC1903 suppressed severe progressive proteinuria with no effect on blood pressure. In AT1R rats at disease onset, TRPC5 inhibition was a cure, with proteinuria reduced to complete remission. This study is the first successful therapeutic intervention working in a targeted, podocyte-protective manner to suppress progressive proteinuric kidney disease in two clinically relevant models.

These data provide strong evidence that the TRPC5 channel, rather than other TRPC channels, is the right therapeutic target for progressive kidney disease. Earlier work had extrapolated from TRPC6 gain-of-function mutations to suggest a role for TRPC6 in acquired (vs. genetically explained) progressive disease such as FSGS (34), but these studies did not take into account TRPC5 channel activity or the knowledge of Rac1 activating mutations, and they did not employ progressive models of FSGS, such as AT1R Tg rats or Dahl S rats. The real-time measurements of channel activity in isolated glomeruli in this study show that increased TRPC5 activity is associated with proteinuric disease progression, while TRPC6 activity appears to be homeostatic. This is supported by the observation that (in addition to gain-of-function mutations) loss-of-function mutations in TRPC6 also lead to FSGS (35). Moreover, the use of two chemically distinct inhibitors, ML204 and AC1903, with the latter being TRPC5-selective, point to TRPC5 as a therapeutic target for FSGS.

A second important consideration is potential toxicities associated with TRPC5 inhibition. Although careful toxicology studies will be needed, several pieces of evidence are encouraging. AT1R Tg rats treated with TRPC5 inhibitor for up to 14 days show no detectable toxicity. Mice lacking TRPC5 show no gross abnormalities, although they exhibit an attenuated fear response due to a developmental defect in the amygdala (36). Studies to date suggest that, outside the brain, the kidney is the tissue of highest TRPC5 activity (11). The in vivo data for both ML204 and AC1903 demonstrate that efficacy in the podocyte may be achievable with relatively low circulating concentrations of drug detected, suggesting that delivery to the kidney filter may be easier than delivery to other tissues. This may translate into greater specificity for a podocyte-targeted therapy, while avoiding on-target or off-target effects in other tissues.

A third important question is determining which patients stand to benefit most from a TRPC5-targeted therapy. While human genetic studies of Rac1-activating mutations in patients with FSGS helped formulate the original therapeutic hypothesis regarding TRPC5 inhibition (6-8), the data in the hypertensive Dahl S rat support a broader applicability of TRPC5 inhibition as a therapeutic strategy for patients with progressive disease more widely attributed to a common TRPC5-triggered pathway. As genomic sequencing studies continue to inform, extend and revise the understanding of susceptibility mutations leading to disease (37), a greater proportion of FSGS may be ultimately explained as "Rac1-TRPC5-activated" FSGS. If so, treatment with a TRPC5 inhibitor may be offered to patients with the appropriate genomic profile. In any case, the salutary effects of treatment with a TRPC5 inhibitor and the elucidation of a detailed pathway leading to FSGS may form the basis for much needed, mechanism-based therapeutic efforts aimed at treating these devastating kidney diseases.

Synthesis of Compounds

The compounds disclosed herein can be synthesized using typical synthetic organic techniques well within the skill of the synthetic organic chemist. Some suggested means for synthesizing compounds disclosed herein include procedures as outlined in Schemes 1 and 2 below and selection of appropriate starting reagents.

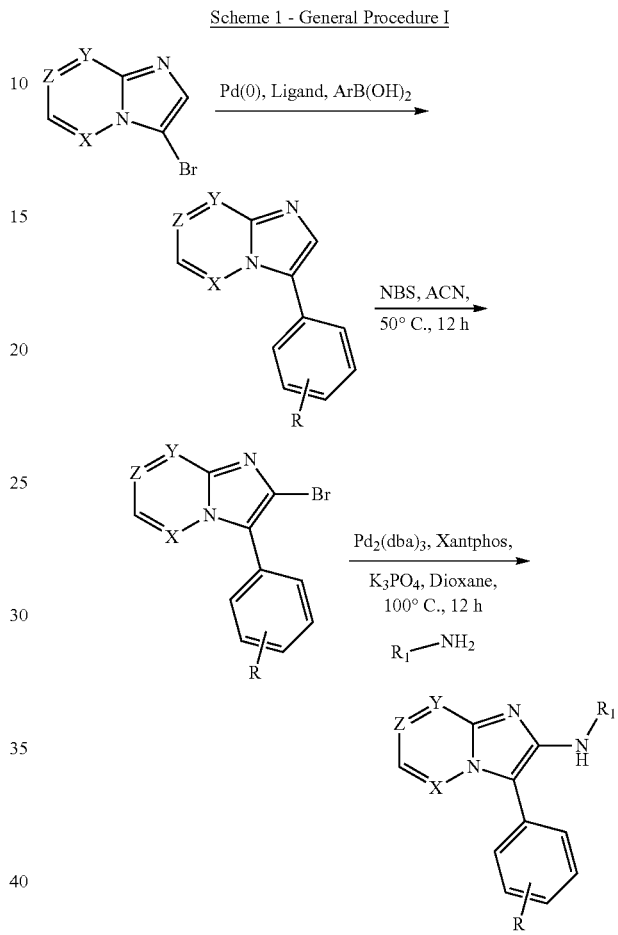

Scheme 1 - General Procedure I

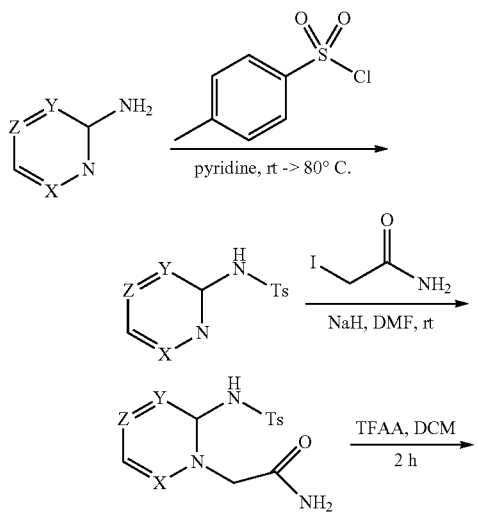

Scheme 2 - General Procedure II

-continued

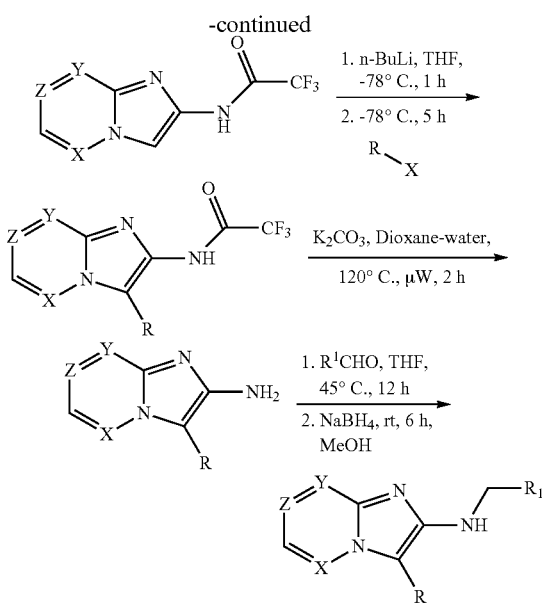

EXAMPLES

Animals and chemicals: Littermates of wild-type (WT) and AT1R TgNeph-hAT1R/185 transgenic (AT1R Tg) rats were housed under a controlled environment with a 12-hour light-dark cycle and access to food and water ad libitum, unless otherwise described. All animal experiments were performed in accordance to the guidelines established and approved by the Animal Care and Use Committee at Brigham and Women's Hospital, Harvard Medical School (Animal Protocol No. 01538). AT1R Tg rats were placed in the Onset cohort when measured proteinuria was >5 mg/day (at approximately 12 weeks of age) on two separate 24-hour urine collections. AT1R Tg rats were placed in the Advanced cohort when measured proteinuria was >25 mg/day (at approximately 18 weeks of age) on two separate 24-hour urine collections. These thresholds were determined after detailed histologic and phenotypic characterization of AT1R Tg rats compared to WT littermates (all combined, n=91 WT rats and n=122 AT1R Tg rats were studied). The Dahl salt-sensitive (S) inbred strain is maintained at University of Mississippi Medical Center (UMMC) and was originally obtained from University of Toledo-College of Medicine (SS/Jr). All animal experiments performed at UMMC were in accordance to the guidelines established and approved by the Institutional Animal Care and Use Committee. Animals used for this studied were provided either low-salt diet [TD7034, 0.3% NaCl and/or high-salt diet [TD94217, 2.0% NaCl] from Harlan Teklad, Madison, Wis. For onset study, at 4 weeks of age, groups of age-matched male S were weaned to the low-salt diet and divided into two groups: vehicle (n=8) and AC1903 groups (n=8). At 6 weeks of age, both groups were placed on the high-salt diet and concurrently treated with either vehicle or AC1903 for 1-week (Onset). For Advanced study, similarly at 4 weeks of age, groups of age-matched male S were weaned to the low-salt diet and divided into two groups: vehicle (n=9) and AC1903 groups (n=11). At 6 weeks of age, both groups were placed on the high-salt diet. At week 7, concurrent with high-salt diet, animals were treated with either vehicle or AC1903 for 1-week (Advanced). At the conclusion of each study, animals were initially anesthetized under 2-3% isoflurane/$O_2$ gas, a catheter attached to a fluid filled pressure transducer was placed in the aorta, isoflurane gas was reduced to 1.5%, and mean arterial pressure was measured for ~5 min period using PowerLab 4/30 system (ADI Instruments, Co) as done previously. All chemicals were purchased from Sigma-Aldrich unless otherwise described.

TRPC4, TRPC5, and TRPC6 inhibition assay: HEK293 whole-cell recordings Whole-cell patch clamp recording was performed 16 h after transfection. The bath solution contained (in mM): 140 NaCl, 5 KCl, 10 HEPES, 2 $MgCl_2$, 2 $CaCl_2$, 10 glucose with pH7.4 adjusted with NaOH. The intracellular solution contained (in mM): 140 KCl, 5 EGTA, 10 HEPES, 2 $MgCl_2$ with pH7.4 adjusted with KOH. The patch pipettes were made using a two-step-protocol (P-97, Sutter Instrument). The pipette resistance was maintained between 4 to 8 MΩ. Once the whole-cell configuration was achieved, cells were clamped at a holding potential of −60 mV, and given a 50 ms ramp stimulation from −100 mV to +100 mV in every 5 s. All currents were filtered at 2 KHz (Axopatch 200B amplifier, Axon Instruments, Union City, Calif.) and digitized at 10 KHz for whole-cell recordings using Axon pCLAMP 10.4. Data were then analyzed using Clampfit 10.4 (Molecular Devices).

Chemical preparation and IP administration: ML204 and AC1903 were prepared from powder in a single batch for each in vivo experiment to avoid variability. Immediately prior to injections, ML204 or AC1903 solution was placed on a heated shaker at 48° C. and 800 RPM. Vehicle was prepared in the same fashion. Injection volume was determined by body weight (2 mL vehicle/compound per kg body weight). Body weight was measured at the time of injection.

Urine collection and assay: For urine collections, rats were housed individually in a metabolic cage supplied with food and water. Urine was collected into a 50 mL falcon tube for 24 hours. Total urine volume was measured and then centrifuged at 3,200 rcf for 10 min at 4° C. Albumin quantification was done according to previously published protocol (11), involving multiple dilutions of urine from each animal compared to Bovine Serum Albumin (BSA) standards. Coumassie Blue stained gels were quantified by densitometry using ImageJ software. As an additional control, the rat ELISA Albumin kit (Exocell) was used for albumin quantification according to the manufacturer's recommendations and yielded the same results. Urine protein was measured using QuanTtest® Red Total Protein Assay System (Quantimetrix, Redondo Beach, Calif.) and expressed as mg protein/24 hours.

Kidney preparation: Rats were anesthetized using pentobarbital sodium (50 mg/kg i.p.) and kidneys were perfused with ice-cold PBS. Kidneys were then perfused with 4% paraformaldehyde and stored in 4% glutaraldehyde solution. After embedding in resin, 1-µm thick sections were cut and stained with toluidine blue. Light microscope images were obtained using a 100× oil lens with a final magnification of 1734×.

Podocyte counting: Podocyte number per glomerulus was counted using the fractionator/disector (16, 17) method on 1-µm thick resin sections. Podocyte nuclei were counted as a surrogate for the number of podocytes assuming one and only one nucleus per podocyte. Briefly, pairs of sections three micrometer apart at 20-µm intervals throughout a glomerulus were imaged. The number of podocyte nuclei profiles seen in the first section (sample section) but not present in the second section (look-up section) was counted. This was repeated for each pair of images from a glomerulus. The number of podocytes per glomerulus was calculated using the equation: Podocyte Number=$(20/3) \times \Sigma Q^-$ where (20/3) is the reciprocal of the fraction of the glomerulus sample and $\Sigma Q^-$ is the sum over all the image pairs from a glomerulus of nuclear profiles from podocytes seen in the sample sections but not in the look-up sections. Five glomeruli per kidney were analyzed and the average number of podocytes per glomerulus calculated.

Pseudocyst volume per glomerulus: The total volume of pseudocyst per glomerulus was measured using the images from the sample sections (see previous paragraph). First the volume density of pseudocysts per glomerulus [($V_v$(pseudocyst/glom)] was measured by the point counting technique (17). Next the volumes of individual glomeruli were measured using the Cavalieri Principle (17). Finally the total volume of pseudocysts per glomerulus was calculated with the equation: Pseudocyst Volume=Vv(pseudocyst/glom)× glomerular volume $\mu m^3$ Five glomeruli per kidney were analyzed and the average volume of pseudocysts per glomerulus was calculated.

HEK293 cell culture and transfection: Transfection of HEK293 cells was carried out using Plus reagent (Invitrogen) and Lipofectamine (Invitrogen) according to standard protocols. For heterologous expression of TRP channels in HEK293 cells, 1 µg of TRPC5-GFP, TRPC6-GFP or TRPC4-GFP plasmids were used to transfect HEK293 cells in a 3.5 cm petri dish where cells were allowed to grow to 80% confluence. Electrophysiology was carried out after 16 h incubation.

Podocyte culture and viral transduction: Immortalized mouse podocytes were cultured as previously described (10, 11). Podocyte viral transduction was performed using lentivirus as previously described (10, 11). Briefly, lentivirus production was carried out in HEK293T cells at 60% confluence, and viral particles were collected two days after transfection and purified by centrifugation at 1,000 rcf for 5 min. Purified lentivirus was frozen at −80° C. until further use. Podocytes were transduced with lentivirus after 7 days of differentiation, and assays were performed 5 days after viral transduction.

Acute glomeruli isolation and $Ca^{2+}$-imaging: WT and AT1R Tg littermates were killed and kidneys were quickly dissected and washed with ice-cold PBS. After isolation using the sieving technique as previously described (11), glomeruli were incubated with the $Ca^{2+}$ indicator Fura2-AM (1 µM; Invitrogen) at 37° C. for 15 min. The extracellular solution for $Ca^{2+}$-imaging contained (in mM) 140 NaCl, 5 KCl, 10 HEPES, 2 $MgCl_2$, 2 $CaCl_2$, 10 glucose, with pH7.4 adjusted with NaOH. Glomerular $Ca^{2+}$-imaging was performed using an inverted microscope (Olympus IX70) with a high-speed CCD camera (Hamamatsu Photonics). Images were taken and analyzed using the Metafluor software (Molecular Devices). It should be noted that Fura-2 is most often taken up by podocytes at the periphery of the isolated glomerulus, but the specificity of recordings in podocytes is best confirmed by patch clamp electrophysiology, as described below.

Glomerular single-channel recordings: Acutely isolated glomeruli were prepared as described above. Single-channel recordings were carried out using an Axopatch 200B and Digidata 1550A (Molecular Devices). Bath and pipette solutions for glomerular single-channel recording contained (in mM) 135 $CH_3SO_3Na$, 5 CsCl, 2 $CaCl_2$, 1 $MgCl_2$, 10 HEPES, and 10 glucose with pH7.4 adjusted with NaOH. Once in the inside-out configuration, the bath solution was replaced by intracellular solution, containing (in mM) 135 $CH_3SO_3Cs$, 10 CsCl, 3 MgATP, 0.2 EGTA, 0.13 $CaCl_2$, and 10 HEPES with pH 7.4 adjusted with CsOH. Patch pipettes, with resistance of 4-8 MΩ, were prepared using a two step-protocol (P-97, Sutter Instrument). Pipettes were fire-polished before use. For inside-out configuration, a giga-seal (>10 GΩ) was established prior to membrane rupture. Data was acquired at 10 kHz sampling frequency, and filtered with low-pass filtering at 1 kHz. Holding membrane potential was at −60 mV. Single-channel analysis was carried out using Clampfit 10.4 software (Molecular Devices).

ROS and cell viability assays: For ROS experiment in FIG. 4A, mature podocytes were cultured as previously described. Cells were incubated with CellRox Deep Red reagent (ThermoFisher) for 30 min at 37° C. Then cells were treated with DMSO, 10 µM angiotensin II, 10 µM angiotensin II with 30 µM AC1903, or 10 µM angiotensin II with 30 µM N-acetyl-L-cysteine (NAC) for 3 hours at 37° C. Cells were washed with PBS twice and fluorescence images were observed using Olympus IX71 microscopy. Fluorescence intensities were then analyzed using ImageJ software.

For experiments in FIG. 4B/C, pCDNA3.1 AT1AR-Δ324 (rat AT1R NM_030985.4) containing HA tag (Plasmid #45635, Addgene) underwent site directed mutagenesis (Agilent) to generate the N111S substitution. For FIG. 4B, differentiated podocytes were transduced with the AT1A-N111S/Δ324 construct in six-well plates. Six days after viral transduction, cells were treated with either vehicle, 30 µM ML204, 30 µM AC1903 or 50 µM NSC23677 for 36 hours. Intracellular production of ROS was measured using a cell-permeable fluorescent dye, 5-(and-6)-chloromethyl-2', 7'-dichlorodihydrofluorescein diacetate, acetyl ester (CM-H2DCFDA, Molecular Probes). Cells were incubated with 5 µM CM-$H_2$DCFDA at 37° C. for 45 min in Hanks' balanced salt solution (HBSS). Cells were then collected, resuspended in HBSS, stained with propidium iodide and the fluorescence intensity was assessed by flow cytometry using MACSQuant Analyzer (Miltenyi Biotec, Bergisch Gladbach, Germany). Living cells, which were PI negative, were selected by FACS gating and the fluorescence of CM-H2DCFDA was recorded on the FL-1 channel (525 nm). For FIG. 4C, differentiated podocytes were transduced with the AT1A-N111S/Δ324 construct in 96 well plates. Six days after transduction, the cells were treated with either vehicle, 30 µM ML204, 30 µM AC1903 or 50 µM NSC23677 for 36 hours. Cell viability assays were performed using Cell Titer-Glo Luminescent Cell Viability Assay kits (Promega) and a luminometer (Veritas Microplate Luminometer) according to the manufacturer's protocol.

Glomerular RNA isolation: Glomerular RNA isolation was performed using the Trizol reagent (Ambion, Life Technologies) according to the manufacturer's protocol. Briefly, acutely isolated glomeruli were homogenized in 1 mL Trizol reagent on ice. After adding 200 µL chloroform, the solution was vigorously mixed and centrifuged 12,000 rcf at 4° C. for 15 min. The aqueous layer was carefully transferred into a new tube. Glomerular RNA was precipitated after adding 500 µL isopropanol by centrifugation 12,000 rcf at 4° C. for 10 min and then washed with 1 mL 70% ethanol. After centrifugation 12,000 rcf at 4° C. for 5 min, the glomerular RNA pellet was allowed to air dry completely and was then dissolved in 15 µL nuclease-free water.

Gene Transcriptional Profiling: cDNA Library Construction: RNA was quantified using the Quant-iT™ RiboGreen® RNA Assay Kit (Thermo Scientific #R11490) and normalized to 5 ng/µL. An automated variant of the Illumina TruSeq™ Stranded mRNA Sample Preparation Kit was used for library preparation from a 200 ng aliquot of RNA. This method preserves strand orientation of the RNA transcript and uses oligo dT beads to select mRNA from the total RNA sample. Following cDNA synthesis and enrichment, cDNA libraries were quantified with qPCR using KAPA Library Quantification Kit for Illumina Sequencing Platforms and then pooled equimolarly.

Illumina Sequencing: Pooled libraries were normalized to 2nM and denatured using 0.1 N NaOH prior to sequencing. Flowcell cluster amplification and sequencing were performed according to the manufacturer's protocols using either the HiSeq 2000 or HiSeq 2500. Each run was a 101 bp paired-end with an eight-base index barcode read. Data was analyzed using the Broad Institute Picard Pipeline, which includes de-multiplexing and data aggregation.

RNA-Seq and Differential Expression Analysis: Reads were aligned to the Rnor_5.0 rat genome using STAR aligner. RSEM v1.3.0 was used to estimate gene expression. FastQC was used to evaluate the quality of raw reads. Low count features were filtered using NOISeq with an expression threshold of >1 count per million per condition (38). Differential expression of individual genes was carried out using DESeq2 (39). Only genes with adjusted p-values <0.05 were considered to be differentially expressed. Gene Ontology analysis was performed using GOrilla. The specific gene ontologies cited in Figure S6: (C) GO:0016491, GO:0015075, GO:0022857, GO:0016614, GO:0008324, GO:0051287, GO:0016829, GO:0016651, GO:0050661; (D) GO:0031589, GO:0007166, GO:0007155, GO:0007229.

Statistical analysis: All statistical analyses were carried out using Graphpad Prism 6 software. Results are presented as Mean±SEM unless otherwise indicated. The comparisons were carried out using the Student's t-test or ANOVA followed by post-hoc comparison using the Bonferroni test. P<0.05 was considered statistically significant.

Synthesis: Synthesis of N-(furan-2-ylmethyl)-3-phenylimidazo[1,2-b]pyridazin-2-amine, 1. Step 1: A 30 mL microwave vial was loaded with bromoimidazo[1,2-b]pyridazine (1 equiv., 1.5 mmol), phenyl boronic acid (1.5 equiv.) and $K_3PO_4$ (2 equiv.) in Dioxane (5 mL). The solution was degassed with $N_2$ gas for 15 min followed by addition of tetrakis(triphenylphosphine)palladium(0) (0.05 equiv.). The reaction was heated in a microwave at 120° C. for 1 hour. Consumption of starting material was checked by TLC. The crude reaction was diluted with ethyl acetate and filtered through a celite bed and was washed with water and brine. The organic layer was dried ($Na_2SO_4$) and evaporated. The product (3-phenylimidazo[1,2-b]pyridazine) was carried on to the next step without further purification. Yield (90% by LCMS). LCMS Analytical: $R_T$=3.029 min, >95% at 254 nm; MS (ESI$^+$) m/z 196.0 [M+H]$^+$.

Step 2: A solution of 3-phenylimidazo[1,2-b]pyridazine (1 equiv.), N-bromosuccinimide (1.5 equiv.), Acetic acid (0.1 equiv.) in ACN (10 ml/mmol) was stirred at 50° C. for 12 h. After completion of reaction, aq. $NaHCO_3$ was added to reaction and the product was fractionated between water and ethyl acetate. The organic layer was dried ($Na_2SO_4$), concentrated and loaded on Normal phase silica gel chromatography to afford the product (2-bromo-3-phenylimidazo[1,2-b]pyridazine) in 0-50% EtOAc:Hexane in 50% yield. LCMS Analytical: $R_T$=4.015 min, >95% yield at 254 nm; MS (ESI$^+$); m/z 273.9 [M+H]$^+$.

Step 3: A solution of 2-bromo-3-phenylimidazo[1,2-b]pyridazine (1 equiv.), furfuryl amine (1.2 equiv.), $K_3PO_4$ (2 equiv.) in anhydrous dioxane (1 ml/0.05 mmol) was degassed with $N_2$ for 10 min followed by addition of $Pd_2(dba)_3$ (0.1 equiv.) and Xanthphos (0.2 equiv.). The reaction was refluxed at 100° C. for 12 h under inert atmosphere. Product formation was confirmed by LCMS. The crude reaction mixture was evaporated and loaded onto Normal phase silica gel chromatography to obtain product (N-(furan-2-ylmethyl)-3-phenylimidazo[1,2-b]pyridazin-2-amine, 1) in 0-80% EtOAc:Hexane. The fractions were evaporated and the solid obtained was recrystallized from DCM by adding cold pentane and subsequent washing with cold pentane. Final product was obtained as a semisolid upon complete drying (20% yield). LCMS Analytical: $R_T$=3.74 min, >95% at 254 nm; MS (ESI$^+$) m/z 291.0 [M+H]$^+$.

Synthesis of 3-(3-chloro-4-methylphenyl)-N-(furan-2-ylmethyl)imidazo[1,2-b]pyridazin-2-amine, 2. Same as Procedure I, Step 1. 3-(4-chloro-3-fluorophenyl)imidazo[1,2-b]pyridazine, 90% yield. LCMS Analytical: $R_T$=2.23 min, >95% at 254 nm; MS (ESI$^+$) m/z 248.0 [M+H]$^+$.

Same as Procedure I, Step 2, 2-bromo-3-(4-chloro-3-fluorophenyl)imidazo[1,2-b] pyridazine with the exception the reaction was refluxed at 80° C. for 48 h, 15% yield. LCMS Analytical: $R_T$=4.18 min., >95% at 254 nm; MS (ESI$^+$) m/z 325.9 [M+H]$^+$.

Same as Procedure I, Step 3. 3-(4-chloro-3-fluorophenyl)-N-(furan-2-ylmethyl) imidazo[1,2-b]pyridazin-2-amine, 18% yield. LCMS Analytical: $R_T$=4.30 min, >95% at 254 nm; MS (ESI$^+$) m/z 343.0 [M+H]$^+$.

Synthesis of 3-(3-chloro-4-methylphenyl)-N-(furan-2-ylmethyl) imidazo[1,2-b] pyridazin-2-amine, 3. Same as Procedure I, Step 1, 3-(3-chloro-4-methylphenyl)imidazo[1,2-b]pyridazine, 90% yield. LCMS Analytical: $R_T$=2.22 min, 95% @254 nm; MS (ESI$^+$) m/z 244.0 [M+H]$^+$.

Same as Procedure I, Step 2, 2-bromo-3-(4-chloro-3-fluorophenyl)imidazo[1,2-b]pyridazine, except reaction was refluxed at 70° C. for 24 h, 20% yield. LCMS Analytical: $R_T$=4.31 min, >95% at 254 nm; MS (ESI$^+$) m/z 322.0 [M+H]$^+$.

Same as Procedure I, Step 3, 3-(3-chloro-4-methylphenyl)-N-(furan-2-ylmethyl)imidazo[1,2-b]pyridazin-2-amine, 25% yield. LCMS Analytical: $R_T$=4.32 min, >95% at 254 nm; MS (ESI$^+$) m/z 339.0 [M+H]$^+$.

Synthesis of 3-benzyl-N-(furan-2-ylmethyl)imidazo[1,2-i]pyridin-2-amine, 4. Uses Procedure II as outlined in above scheme. Step 1: 2-aminopyridine (1 eq.) in pyridine (4 ml/1 g) was treated portion-wise with tosyl chloride (1.1 eq.) at RT. After completion of addition, the reaction was subjected to heating at 80° C. for 12 h. After cooling to rt, pyridine was evaporated from crude. The resulting crude mixture was diluted with ethyl acetate (8 ml/g), stirred for 5 minutes than water (8 m/g) was added. This solution was stirred for 30 min to break down solids. The resulting solids were filtered and washed with cold water and cold ethyl acetate. Filter cake was dried to obtain product as white solid, 4-methyl-N-(pyridin-2-yl) benzenesulfonamide (19% yield). LCMS Analytical: $R_T$=2.85 min, >95% at 254 nm; MS (ESI$^+$) m/z 249.0 [M+H]$^+$.

Step 2: NaH (1.2 eq.) in DMF (8 m/g of starting material) was treated portion-wise with 4-methyl-N-(pyridin-2-yl) benzenesulfonamide (1 eq.) at 0° C. After stirring for 30 minutes, iodoacetamide (1 equiv.) was added in single addition. The reaction was stirred at RT overnight under inert gas atmosphere. The DMF was evaporated under vacuum. The crude reaction mixture was diluted with ethyl acetate (10 m/g) followed by water (2 ml/g) and then was stirred for 30 min to break solids. The solids were filtered and dried to afford product, 2-(2-((4-methylphenyl)sulfonamido)pyridin-1(2H)-yl) acetamide, 56% yield. LC Analytical: $R_T$=1.83 min, >95% at 254 nm.

Step 3: Trifluoroacetic anhydride (3.75 ml/g) was added in a solution of 2-(2-((4-methylphenyl)sulfonamido)pyridin- 1(2H)-yl) acetamide in DCM (10 ml/g). The reaction mixture was stirred at RT for 2 h. Solvent was evaporated and diluted with ethyl acetate. Saturated NaHCO$_3$ was added until effervesces seized. Organic phase was separated, dried (Na$_2$SO$_4$), evaporated and loaded on Normal phase flash chromatography to afford product in 0-80% EtOAc:Hexane. Product was obtained as brown solid, 2,2,2-trifluoro-N-(imidazo[1,2-a]pyridin-2-yl)acetamide, 57% yield. LCMS Analytical: R$_T$=1.88 min, >95% at 254 nm; MS (ESI$^+$) m/z 230.0 [M+H]$^+$.

Step 4: 2,2,2-trifluoro-N-(imidazo[1,2-a]pyridin-2-yl)acetamide (1 equiv.) in THF (1 ml/0.1 mmol) was treated portion-wise with n-BuLi (1.5 equiv., 2.5 M in hexanes) at −78° C. After stirring for 1 hour at −78° C., benzyl bromide (1.2 equiv.) was added and the mixture was stirred at −78° C. for 5 h then gradually allowed to reach RT overnight. THF was removed from crude, and then worked up with water and ethyl acetate. Organic layer was separated dried (Na$_2$SO$_4$) and evaporated. Resulting crude was purified with reverse phase chromatography under a gradient of 0-100% ACN:Water. Product was obtained as yellow solid, N-(3-benzylimidazo[1,2-a]pyridin-2-yl)-2,2,2-trifluoroacetamide, 32% yield. LCMS Analytical: R$_T$=2.633 min, >95% yield; MS (ESI$^+$) m/z 320.0 [M+H]$^+$.

Step 5: N-(3-benzylimidazo[1,2-a]pyridin-2-yl)-2,2,2-trifluoroacetamide (1 eq.) and K$_2$CO$_3$ (5 equiv.) in dioxane:water (4:1) were subjected to Microwave irradiation at 120° C. for 2 h. Solvent was evaporated and the product was partitioned between water and ethyl acetate. Organic layer was separated dried (Na$_2$SO$_4$) and evaporated. Resulting product was used as such, 3-benzylimidazo[1,2-a] pyridin-2-amine, 90% yield. LCMS Analytical: R$_T$=1.77 min, >95% at 254 nm; MS (ESI$^+$) m/z 224.1 [M+H]$^+$.

Step 6: 3-benzylimidazo[1,2-a]pyridin-2-amine (1 eq.) and furfurylaldehyde (1.5 eq.) in THF were stirred at 45° C. for 12 h under inert atmosphere. The crude material was brought to RT, followed by addition of NaBH$_4$ (2 eq.) and MeOH (10 eq.) and stirred for 6 h. The reaction mixture was worked up with NH$_4$Cl solution and ethyl acetate. Organic layer was evaporated and purified with reverse phase chromatography under a gradient of 0-100% ACN:Water. Product was obtained as yellow semi solid, 3-benzylimidazo[1,2-a]pyridin-2-amine, 20% yield. LCMS Analytical: R$_T$=1.94 min, >95% at 254 nm; MS (ESI$^+$) m/z 304.1 [M+H]$^+$.

4-methyl-N-(pyridin-2-yl)benzenesulfonamide. In a 25 mL RBF fitted with magnetic stir bar, 2-amino pyridine (1.0 g, 10.6 mmol) in pyridine (5 mL) was treated portion wise with Tosyl chloride (2.02 g, 10.6 mmol) at rt. After completion of addition reaction was subjected to heating at 80° C. for 12 h. Pyridine was evaporated from crude. Resulting crude was diluted with ethyl acetate (8 mL), stirred for 5 minutes than water (8 mL) was added. This solution was stirred for 30 min to break down solids. The resulting solids were filtered and washed with cold water and cold ethyl acetate. Filter cake was dried to obtain product as white solid. (0.91 g, 35%). LCMS: R$_T$=2.03 min., >98% @215 and 254 nm, m/z=249.0 [M+H]$^+$. $^1$H NMR (499 MHz, CDCl$_3$) δ 8.17-8.12 (m, 1H), 7.74 (d, J=8.2 Hz, 2H), 7.61 (ddd, J=8.9, 7.2, 1.8 Hz, 1H), 7.31 (d, J=8.9 Hz, 1H), 7.20 (d, J=8.1 Hz, 2H), 6.75 (t, J=6.5 Hz, 1H), 2.33 (s, 3H). $^{13}$C NMR (126 MHz, CDCl$_3$) δ 158.53, 146.91, 146.01, 144.22, 142.41, 133.46, 132.86, 130.65, 129.69, 119.20, 118.26, 25.30.

(Z)-2-(2-(tosylimino)pyridin-1(2H)-yl)acetamide. In a 25 mL RBF fitted with magnetic stir bar, NaH (0.13 g, 3.9 mmols) in DMF (8 mL) was treated portion wise with 4-methyl-N-(pyridin-2-yl)benzenesulfonamide (0.9 g, 3.62 mmol) at 0° C. After stirring for 30 minutes, iodoacetamide (0.67 g, 3.62 mmol) was added in single addition. The reaction was stirred at rt overnight under inert gas atmosphere. DMF was evaporated under vacuum. Crude was diluted with ethyl acetate (10 mL) followed by water (2 mL). It was stirred for 30 min to break solids. Which were filtered and dried to afford product. (0.62 g, 56%). LCMS: R$_T$=1.80 min., >98% @215 and 254 nm, m/z=307.0 [M+H]$^+$.

2,2,2-trifluoro-N-(imidazo[1,2-a]pyridin-2-yl)acetamide. In a 25 mL RBF fitted with magnetic stir bar, trifluro acetic anhydride (3.75 mL) was added to a solution of 2-(2-((4-methylphenyl) sulfonamido) pyridin-1(2H)-yl) acetamide (1.0 g, 3.2 mmol) in DCM (10 mL). It was stirred at rt for 2 h. Solvent was evaporated and diluted with ethyl acetate (100 mL). Saturated sodium bicarbonate was added until effervesces seized. Organic phase was separated, dried over sodium sulphate, evaporated and loaded on Normal phase flash chromatography to afford product in 0-80% EtOAc: Hexane. Product was obtained as brown solid. (0.41 g, 57%) LCMS: R$_T$=1.91 min., >98% @215 and 254 nm, m/z=231.0 [M+H]$^+$. $^1$H NMR (499 MHz, DMSO) δ 12.45 (s, 1H), 8.61 (d, J=6.7 Hz, 1H), 8.24 (s, 1H), 7.51 (d, J=9.0 Hz, 1H), 7.32-7.28 (m, 1H), 6.95 (t, J=6.7 Hz, 1H). $^{13}$C NMR (126 MHz, DMSO) δ 154.56, 154.26, 141.68, 139.74, 127.55, 125.91, 117.34, 116.15, 115.05, 112.86, 103.00.

N-(3-benzylimidazo[1,2-a]pyridin-2-yl)-2,2,2-trifluoroacetamide. In a 25 mL RBF fitted with magnetic stir bar, 2,2,2-trifluoro-N-(imidazo[1,2-a] pyridin-2-yl) acetamide (1.5 g, 6.5 mmol) in THF (50 mL) was treated portion wise with n-Buli (3.5 mL,14.3 mmol) at −78° C. under inert atmosphere. After stirring for 1 hour at −78° C., benzyl bromide (1.3 g, 7.8 mmol) was added to it. Stirred at −78° C. for 5 h then gradually allowed to reach RT overnight. THF was removed from crude, crude was worked up with water and ethyl acetate. Organic layer was separated dried over sodium sulphate and evaporated. Resulting crude was purified with reverse phase chromatography under a gradient of 0-100% ACN:Water. Product was obtained as yellow solid. (0.65 g, 32%). LCMS: R$_T$=2.58 min., >98% @215 and 254 nm, m/z=320.0 [M+H]$^+$. $^1$H NMR (499 MHz, DMSO) δ 11.68 (s, 1H), 8.17 (d, J=6.8 Hz, 1H), 7.57 (d, J=9.0 Hz, 1H), 7.33-7.23 (m, 3H), 7.19 (t, J=7.7 Hz, 3H), 6.94 (t, J=6.7 Hz, 1H), 4.28 (s, 2H). $^{13}$C NMR (126 MHz, DMSO) δ 137.41, 129.01, 128.56, 127.00, 125.31, 124.85, 113.13, 28.41.

3-benzylimidazo[1,2-a]pyridin-2-amine. In a 10 mL microwave vial, N-(3-benzylimidazo[1,2-a]pyridin-2-yl)-2,2,2-trifluoroacetamide (0.10 g, 0.31 mmol) and K$_2$CO$_3$ (1.5 g, 1.56 mmol) in Dioxane:Water (4:1, 0.2 mL) were subjected to Microwave irradiation at 120° C. for 2 h. Solvent was evaporated. Product was partitioned between water and ethyl acetate. Organic layer was separated dried over sodium sulphate and evaporated. Resulting product was used as such. (63 mg, 90%). LCMS: R$_T$=1.76 min., >98% @215 and 254 nm, m/z=224.1 [M+H]$^+$.

3-benzyl-N-(pyridin-3-yl)imidazo[1,2-a]pyridin-2-amine (6). In a 10 mL seal-tube, solution of 3-benzylimidazo[1,2-a]pyridin-2-amine, 3-bromopyridine (50.0 mg, 0.22 mmol) and K$_3$PO$_4$ (142.0 mg, 0.672 mmol) in anhydrous DMF (3 mL) was degassed with nitrogen for 10 min followed by addition of Pd$_2$(dba)$_3$ (20.4 mg, 0.02 mmol) and Xanthphos (25 mg, 0.044 mmol). The reaction crude was refluxed at 90° C. for 12 h under inert gas environment. Product formation was confirmed by LCMS. The crude was evaporated and loaded onto Normal phase silica gel chromatography to obtain product in 0-80% EtOAc:Hexane. (18 mg, 26%). LCMS: R$_T$=1.68 min., >98% @215 and 254 nm, m/z=301.2

[M+H]⁺. ¹H NMR (499 MHz, CDCl₃) δ 8.29 (s, 1H), 8.10 (d, J=4.0 Hz, 1H), 7.73 (t, J=9.0 Hz, 2H), 7.56 (d, J=8.9 Hz, 1H), 7.32 (dd, J=15.6, 8.3 Hz, 2H), 7.21-7.12 (m, 4H), 6.78 (t, J=6.8 Hz, 1H), 5.83 (s, 1H), 4.26 (s, 2H). ¹³C NMR (126 MHz, CDCl₃) δ 142.90, 142.43, 140.92, 140.54, 138.21, 136.14, 129.92, 129.09, 128.53, 128.09, 127.15, 123.67, 123.45, 122.65, 121.85, 116.35, 112.16, 108.62, 29.08.

3-(4-fluorobenzyl)-N-(furan-2-ylmethyl)imidazo[1,2-a]pyridin-2-amine (5). In a 25 mL RBF fitted with magnetic stir bar and condenser, 3-(4-fluorobenzyl)imidazo[1,2-a]pyridin-2-amine (70.0 mg, 0.28 mmol) and furufuraldehyde (35 µL, 0.43 mmol) in THF (4 mL) were stirred at 45° C. for 12 h under inert atmosphere. Crude was brought to rt, followed by addition of NaBH₄ (26 mg, 0.72 mmol) and MeOH (0.5 mL) and stirred for 6 h. Crude was worked up with ammonium chloride solution and ethyl acetate. Organic layer was evaporated and purified with reverse phase chromatography under a gradient of 0-100% ACN:Water. Product was obtained as yellow semi solid. LCMS: $R_T$=1.94 min., >98% @215 and 254 nm, m/z=322.1 [M+H]⁺. ¹H NMR (499 MHz, CDCl₃) δ 7.56 (d, J=6.7 Hz, 1H), 7.48 (d, J=8.9 Hz, 1H), 7.35 (d, J=0.9 Hz, 1H), 7.10-7.03 (m, 3H), 6.96 (t, J=8.6 Hz, 2H), 6.68 (t, J=6.4 Hz, 1H), 6.33-6.30 (m, 1H), 6.23 (d, J=2.8 Hz, 1H), 4.66 (d, J=4.1 Hz, 2H), 4.12 (s, 2H), 3.86 (s, 1H). ¹³C NMR (126 MHz, CDCl₃) δ 153.58, 149.56, 142.51, 141.82, 132.43, 132.40, 129.36, 129.29, 122.19, 121.64, 115.78, 115.61, 115.13, 111.43, 110.29, 106.88, 41.94, 27.93. Syncropath % inhibition TRPC5 @3 µM: 0.8874.

ethyl 2-(2-iminopyridin-1(2H)-yl)acetate. pyridin-2-amine (3.0 g, 31.9 mmol) and ethyl bromoacetate (8 mL) in a 25 mL RBF were stirred at rt for 18 h. Crude was filtered, and solids collected were washed with DCM and dried to afford desired product as an HBr salt. (6.2 g, 74.5%) LCMS: $R_T$=0.53 min., >98% @215 and 254 nm, m/z=181.1 [M+H]⁺. 1H NMR (499 MHz, DMSO) δ 8.72 (s, 1.8H), 8.08 (d, J=6.5 Hz, 1H), 7.93 (t, J=7.8 Hz, 1H), 7.20 (d, J=8.9 Hz, 1H), 6.94 (t, J=6.7 Hz, 2H), 4.20 (q, J=7.1 Hz, 2H), 1.25 (t, J=7.1 Hz, 3H). ¹³C NMR (126 MHz, DMSO) δ 166.37, 155.12, 143.36, 140.89, 115.45, 113.14, 62.44, 54.22, 40.50, 40.33, 40.26, 40.17, 40.00, 39.83, 39.67, 39.50, 14.43.

2-chloroimidazo[1,2-a]pyridine. In a 25 mL RBF fitted with magnetic stir bar and condenser, ethyl 2-(2-iminopyridin-1(2H)-yl) acetate (6 g, 33.3 mmol) in POCl₃ (12 mL), was refluxed at 105° C. for 3 h. POCl₃ was removed under vacuum, the crude was neutralized with ice water and ammonium hydroxide solution until pH-8. Product was extracted with DCM, dried over MgSO₄, evaporated and used as such. (3.5 g, crude) LCMS: $R_T$=1.64 min., >98% @215 and 254 nm, m/z=153.0 [M+H]⁺. ¹H NMR (499 MHz, DMSO) δ 8.51 (d, J=6.7 Hz, 1H), 8.06 (s, 1H), 7.54 (d, J=9.0 Hz, 1H), 7.36-7.31 (m, 1H), 6.99 (t, J=6.4 Hz, 1H). ¹³C NMR (126 MHz, DMSO) δ 143.51, 134.18, 127.12, 126.24, 116.51, 113.44, 109.45.

2-chloro-3-iodoimidazo[1,2-a]pyridine. In a 25 mL RBF fitted with magnetic stir bar, NIS (0.88 g, 3.94 mmol) was added to a stirred solution of 2-chloroimidazo[1,2-a]pyridine (0.50 g, 3.29 mmol) in ACN (10 mL) and stirred at rt for 2 h. The crude was concentrated under vacuum, the product was separated between DCM and brine. Organic layer was separated, dried over MgSO₄, evaporated and purified by normal phase flash chromatography (0-80% EtOAc:Hexane). (0.6 g, 65%). LCMS: $R_T$=2.29 min., >98% @215 and 254 nm, m/z=278.9 [M+H]⁺. ¹H NMR (499 MHz, CDCl₃) δ 8.04 (d, J=6.9 Hz, 1H), 7.50 (d, J=9.0 Hz, 1H), 7.30-7.26 (m, 1H), 6.97 (td, J=6.9, 1.0 Hz, 1H). ¹³C NMR (126 MHz, CDCl₃) δ 146.61, 141.49, 126.57, 126.38, 126.22, 126.11, 116.98, 116.93, 113.91.

3-benzyl-2-chloroimidazo[1,2-a]pyridine. In a 15 mL seal-tube, solution of 2-chloro-3-iodoimidazo[1,2-a]pyridine (200.0 mg, 0.72 mmol), Cs₂CO₃ (702.0 mg, 2.16 mmol) and benzyl boronic acid (195.0 mg, 1.44 mmole) in THF (4 mL) was degassed with nitrogen for 10 min followed by addition of Pd(OAc)₂ (16.1 mg, 0.072 mmol) and TPP (37 mg, 0.14 mmol). The reaction crude was refluxed at 100° C. for 6 h under inert gas environment. Product formation was confirmed by LCMS. The crude was evaporated and loaded onto Normal phase silica gel chromatography to obtain product in 0-100% EtOAc:Hexane. (71 mg, 40%). LCMS: $R_T$=2.49 min., >98% @215 and 254 nm, m/z=243.0 [M+H]⁺. ¹H NMR (499 MHz, CDCl₃) δ 7.71 (d, J=6.9 Hz, 1H), 7.57 (d, J=9.1 Hz, 1H), 7.34-7.29 (m, 2H), 7.26 (t, J=7.3 Hz, 1H), 7.19 (d, J=8.1 Hz, 3H), 6.77 (tt, J=7.1, 3.6 Hz, 1H), 4.33 (s, 2H).

3-benzyl-2-(pyrrolidin-1-yl)imidazo[1,2-a]pyridine (7). In a 10 mL seal-tube, solution of 3-benzyl-2-chloroimidazo[1,2-a]pyridineb (50.0 mg, 0.206 mmol), pyrrolidine (25 µL, 0.309 mmol) and NaOtBu (56.0 mg, 0.618 mmol) in anhydrous toluene (1.5 mL) was degassed with nitrogen for 10 min followed by addition of Pd₂(dba)₃ (18.0 mg, 0.026 mmol) and JohnPhos (12 mg, 0.041 mmol). The reaction crude was refluxed at 110° C. for 16 h under inert gas environment in a 10 mL sealtube. The crude was evaporated and loaded onto Normal phase silica gel chromatography to obtain product in 0-60% EtOAc:Hexane. (14 mg, 25%). LCMS: $R_T$=2.11 min., >98% @215 and 254 nm, m/z=278.1 [M+H]⁺. ¹H NMR (499 MHz, CDCl₃) δ 7.54 (d, J=6.7 Hz, 1H), 7.45 (d, J=8.8 Hz, 1H), 7.30-7.27 (m, 2H), 7.23 (t, J=6.6 Hz, 1H), 7.16 (d, J=7.3 Hz, 2H), 7.04 (dd, J=11.5, 4.2 Hz, 1H), 6.61 (t, J=6.7 Hz, 1H), 4.41 (s, 2H), 3.60 (t, J=6.5 Hz, 4H), 1.98 (t, J=6.5 Hz, 4H). ¹³C NMR (126 MHz, CDCl₃) δ 151.57, 142.44, 138.41, 128.76, 127.62, 126.52, 121.86, 121.51, 114.29, 110.93, 101.23, 49.65, 29.81, 25.49. Syncropath % inhibition TRPC5 @3 µM: 0.334

REFERENCES

1. Jha et al., Chronic kidney disease: global dimension and perspectives. *Lancet* 382, 260-272 (2013).
2. Inrig et al., The landscape of clinical trials in nephrology: a systematic review of Clinicaltrials.gov. *Am J Kidney Diseases* 63, 771-780 (2014).
3. D'Agati, et al., Focal segmental glomerulosclerosis. *New Engl J Med* 365, 2398-2411 (2011).
4. Greka, and Mundel, Cell biology and pathology of podocytes. *Annual Rev Physiol* 74, 299-323 (2012).
5. Brown, et al., Genetic testing for nephrotic syndrome and FSGS in the era of next-generation sequencing. *Kidney Int* 85, 1030-1038 (2014).
6. Akilesh et al., Arhgap24 inactivates Rac1 in mouse podocytes, and a mutant form is associated with familial focal segmental glomerulosclerosis. *J Clin Invest* 121, 4127-4137 (2011).
7. Gee et al., ARHGDIA mutations cause nephrotic syndrome via defective RHO GTPase signaling. *J Clin Invest* 123, 3243-3253 (2013).
8. Yu et al., A role for genetic susceptibility in sporadic focal segmental glomerulosclerosis. *J Clin Invest* 126, 1603 (2016).
9. Bezzerides, et al., Rapid vesicular translocation and insertion of TRP channels. *Nature Cell Biol* 6, 709-720 (2004).

10. Tian et al., Antagonistic regulation of actin dynamics and cell motility by TRPC5 and TRPC6 channels. *Sci Signal* 3, ra77 (2010).
11. Schaldecker et al., Inhibition of the TRPC5 ion channel protects the kidney filter. *J Clin Invest* 123, 5298-5309 (2013).
12. Wieder and Greka, Calcium, TRPC channels, and regulation of the actin cytoskeleton in podocytes: towards a future of targeted therapies. *Pediatr Nephrol*, (2015).
13. Hoffmann, et al., Angiotensin II Type 1 Receptor Overexpression in Podocytes Induces Glomerulosclerosis in Transgenic Rats. *J Am Soc Nephrol* 15, 1475-1487 (2004).
14. Hsu et al., Mechanisms of angiotensin II signaling on cytoskeleton of podocytes. *J Mol Med* 86, 1379-1394 (2008).
15. Miller et al., Identification of ML204, a novel potent antagonist that selectively modulates native TRPC4/C5 ion channels. *J Biol Chem* 286, 33436-33446 (2011).
16. Steffes, et al., Glomerular cell number in normal subjects and in type 1 diabetic patients. *Kidney Int* 59, 2104-2113. (2001).
17. Weins et al., Dendrin ablation prolongs life span by delaying kidney failure. *Am J Pathol* 185, 2143-2157 (2015).
18. Kriz and Lemley, A potential role for mechanical forces in the detachment of podocytes and the progression of CKD. *J Am Soc Nephrol* 26, 258-269 (2015).
19. Richter, et al., Riluzole activates TRPC5 channels independently of PLC activity. *Br J Pharmacol* 171, 158-170 (2014).
20. Hofmann et al., Direct activation of human TRPC6 and TRPC3 channels by diacylglycerol. *Nature* 397, 259-263 (1999).
21. Freichel et al., Lack of an endothelial store-operated Ca2+ current impairs agonist-dependent vasorelaxation in TRP4-/- mice. *Nature Cell Biol* 3, 121-127 (2001).
22. Richter, et al., Clemizole hydrochloride is a novel and potent inhibitor of transient receptor potential channel TRPC5. *Mol Pharmacol* 86, 514-521 (2014).
23. Buvall et al., Synaptopodin Is a Coincidence Detector of Tyrosine versus Serine/Threonine Phosphorylation for the Modulation of Rho Protein Crosstalk in Podocytes. *J Am Soc Nephrol* (2016).
24. Wu et al., Subcellular targeting of oxidants during endothelial cell migration. *J Cell Biol* 171, 893-904 (2005).
25. Pierce, et al., Seven-transmembrane receptors. *Nat Rev Mol Cell Biol* 3, 639-650 (2002).
26. Sharma, et al. "Adiponectin regulates albuminuria and podocyte function in mice." J Clin Invest 118(5): 1645-1656 (2008).
27. You, et al. "Metabolomics Reveals a Key Role for Fumarate in Mediating the Effects of NADPH Oxidase 4 in Diabetic Kidney Disease." *J Am Soc Nephrol* 27(2): 466-481 (2016).
28. Gee et al., Mutations in EMP2 cause childhood-onset nephrotic syndrome. *Am J Hum Genet* 94, 884-890 (2014).
29. Gee et al., KANK deficiency leads to podocyte dysfunction and nephrotic syndrome. *J Clin Invest* 125, 2375-2384 (2015).
30. Rapp, Dahl salt-susceptible and salt-resistant rats. A review. *Hypertens* 4, 753-763 (1982).
31. Zicha et al., Age-dependent salt hypertension in Dahl rats: fifty years of research. *Physiol Res* 61 Suppl 1, S35-87 (2012).
32. Garrett, et al., Time-course genetic analysis of albuminuria in Dahl salt-sensitive rats on low-salt diet. *J Am Soc Nephrol* 14, 1175-1187 (2003).
33. Yamada et al., Mechanism underlying the efficacy of combination therapy with losartan and hydrochlorothiazide in rats with salt-sensitive hypertension. *Hypertens Res* 34, 809-816 (2011).
34. Eckel, et al. "TRPC6 Enhances Angiotensin Il-induced Albuminuria." J Am Soc Nephrol 22(3): 526-535 (2011).
35. Riehle et al., TRPC6 G757D Loss-of-Function Mutation Associates with FSGS. *J Am Soc Nephrol* 27, 2771-2783 (2016).
36. Riccio et al., Essential role for TRPC5 in amygdala function and fear-related behavior. *Cell* 137, 761-772 (2009).
37. Lek et al., Analysis of protein-coding genetic variation in 60,706 humans. *Nature* 536, 285-291 (2016).
38. Tarazona et al., Data quality aware analysis of differential expression in RNA-seq with NOISeq R/Bioc package. *Nucleic Acids Res* 43, e140 (2015).
39. Love, et al., Moderated estimation of fold change and dispersion for RNA-seq data with DESeq2. *Genome Biol* 15, 550 (2014).

What is claimed:

1. A compound, or pharmaceutically acceptable salt thereof, having a structure of Formula (II):

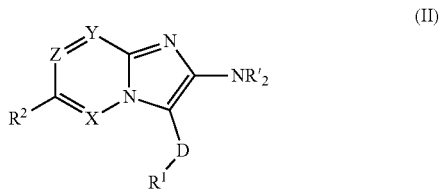

wherein

X, Y, and Z are each $CR^2$;

D is a bond or $C_1$-$C_4$alkylene;

$R^1$ comprises $C_1$-$C_4$ alkyl, $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O, and $R^1$ is optionally substituted with one, two, or three substituents selected from halo, CN, $C_1$-$C_6$alkyl, $C_1$-$C_6$haloalkyl, and $C_3$-$C_6$cycloalkyl;

each $R^2$ is independently H, halo, $C_1$-$C_5$alkyl, $C_1$-$C_5$haloalkyl, or $C_3$-$C_{12}$cycloalkyl; and each R' together with the nitrogen atom to which they are attached form a 3-10 membered heterocycloalkyl containing 0 to 3 additional ring heteroatoms selected from N, S, and O, and the heterocycloalkyl is optionally substituted with one, two or three substituents selected from halo, CN, $C_1$-$C_6$alkyl, $C_1$-$C_6$haloalkyl, and $C_3$-$C_6$cycloalkyl.

2. The compound of claim 1, wherein X, Y, and Z are each $CR^2$ and $R^1$ is $C_6$-$C_{12}$ aryl, $C_3$-$C_{10}$ heteroaryl containing 1 to 3 ring heteroatoms selected from N, S, and O, $C_3$-$C_{12}$ cycloalkyl, or $C_3$-$C_{10}$ heterocycloalkyl containing 1 to 3 ring heteroatoms selected from N, S, and O.

3. The compound of claim 1, wherein each $R^2$ is H.

4. The compound of claim 1, wherein at least one $R^2$ is halo.

5. The compound of claim 1, wherein D is a bond.

6. The compound of claim 1, wherein D is $C_1$-$C_4$alkylene.

7. The compound of claim 6, wherein D is $CH_2$ or $CH_2CH_2$.

8. The compound of claim 1, wherein —$NR'_2$ forms a 5-6 membered heterocycloalkyl ring.

9. The compound of claim 8, wherein the —$NR'_2$ heterocycloalkyl ring is substituted with one, two or three substituents selected from halo, CN, $C_1$-$C_6$alkyl, $C_1$-$C_6$haloalkyl, and $C_3$-$C_6$cycloalkyl.

10. The compound of claim 1, wherein $R^1$ comprises phenyl.

11. The compound of claim 1, wherein $R^1$ comprises furyl, thienyl, thiazolyl, oxazolyl, oxadiazolyl, thiadiazolyl, pyridyl, pyridazinyl, pyrimidinyl, pyrazinyl, pyranyl, tetrahydrofuryl, tetrahydropyranyl, morpholinyl, piperadinyl, thiomorpholinyl, or piperazinyl.

12. A compound which is compound 7:

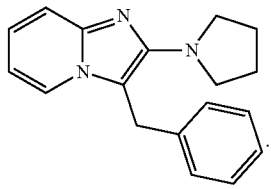

(7)

13. A method of treating a subject suffering from kidney disease comprising administering a therapeutically effective amount of the compound of claim 1 to the subject.

14. A method of treating a subject suffering from a TRPC5-mediated disease comprising administering to the subject a therapeutically effective amount of the compound of claim 1.

* * * * *